(12) United States Patent
Long et al.

(10) Patent No.: US 10,118,877 B2
(45) Date of Patent: Nov. 6, 2018

(54) METAL-ORGANIC FRAMEWORKS FOR AROMATIC HYDROCARBON SEPARATIONS

(71) Applicant: The Regents of the University of California, Oakland, CA (US)

(72) Inventors: Jeffrey R. Long, Oakland, CA (US); Eric D. Bloch, Cambridge, MA (US); Matthew Kapelewski, Berkeley, CA (US); Miguel Carlos I. Gonzalez, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 13 days.

(21) Appl. No.: 14/957,494

(22) Filed: Dec. 2, 2015

(65) Prior Publication Data

US 2016/0159713 A1 Jun. 9, 2016

Related U.S. Application Data

(60) Provisional application No. 62/087,201, filed on Dec. 3, 2014.

(51) Int. Cl.
| | |
|---|---|
| *C07F 15/00* | (2006.01) |
| *C07C 7/12* | (2006.01) |
| *C07F 15/06* | (2006.01) |
| *B01J 20/22* | (2006.01) |
| *B01D 53/02* | (2006.01) |
| *C10G 25/00* | (2006.01) |
| *B01D 15/08* | (2006.01) |
| *B01D 15/38* | (2006.01) |
| *B01D 53/04* | (2006.01) |
| *B01D 53/047* | (2006.01) |

(52) U.S. Cl.
CPC ............... *C07C 7/12* (2013.01); *B01D 15/08* (2013.01); *B01D 15/3828* (2013.01); *B01D 53/02* (2013.01); *B01D 53/04* (2013.01); *B01J 20/226* (2013.01); *C07F 15/065* (2013.01); *C10G 25/003* (2013.01); *B01D 53/047* (2013.01); *B01D 53/0462* (2013.01); *B01D 2253/204* (2013.01); *B01D 2257/7027* (2013.01)

(58) Field of Classification Search
CPC ...... C07F 15/065; B01J 2/226; B01J 31/1691; C07C 7/12
USPC ........................................................ 556/147
See application file for complete search history.

(56) References Cited

U.S. PATENT DOCUMENTS

| | | |
|---|---|---|
| 2,684,967 A | 7/1954 | Berg |
| 4,532,225 A | 7/1985 | Tsao |
| 5,064,804 A | 11/1991 | Soo |
| 5,160,500 A | 11/1992 | Chu |
| 5,208,335 A | 5/1993 | Ramprasad |
| 5,648,508 A | 7/1997 | Yaghi |
| 5,733,505 A | 3/1998 | Goldstein |
| 5,779,904 A | 7/1998 | Ruderman |
| 6,479,447 B2 | 11/2002 | Bijl |
| 6,501,000 B1 | 12/2002 | Stibrany |
| 6,617,467 B1 | 9/2003 | Mueller |
| 6,624,318 B1 | 9/2003 | Mueller |
| 6,686,428 B2 | 2/2004 | Zhang |
| 6,893,564 B2 | 5/2005 | Mueller |
| 6,929,679 B2 | 8/2005 | Mueller |
| 6,930,193 B2 | 8/2005 | Yaghi |
| 7,196,210 B2 | 3/2007 | Yaghi |
| 7,202,385 B2 | 4/2007 | Mueller |
| 7,229,943 B2 | 6/2007 | Gibson |
| 7,279,517 B2 | 10/2007 | Mueller |
| 7,309,380 B2 | 12/2007 | Mueller |
| 7,343,747 B2 | 3/2008 | Mueller |
| 7,411,081 B2 | 8/2008 | Mueller |
| 7,524,444 B2 | 4/2009 | Hesse |
| 7,582,798 B2 | 9/2009 | Yaghi |
| 7,637,983 B1 | 12/2009 | Liu |
| 7,815,716 B2 | 10/2010 | Mueller |
| 8,343,260 B2 | 1/2013 | Omary |
| 8,480,955 B2 | 7/2013 | Yaghi |
| 8,501,150 B2 | 8/2013 | Schubert |
| 8,518,264 B2 | 8/2013 | Kiener |
| 8,524,932 B2 | 9/2013 | Leung |
| 8,709,134 B2 | 4/2014 | Yaghi |
| 8,735,161 B2 | 5/2014 | Yaghi |
| 8,742,152 B2 | 6/2014 | Yaghi |
| 9,078,922 B2 | 7/2015 | Yaghi |
| 2003/0004364 A1 | 1/2003 | Yaghi |
| 2003/0078311 A1 | 4/2003 | Muller |
| 2003/0148165 A1 | 8/2003 | Muller |

(Continued)

FOREIGN PATENT DOCUMENTS

| | | |
|---|---|---|
| CN | 1910191 A | 2/2007 |
| CN | 101270094 A | 9/2008 |

(Continued)

OTHER PUBLICATIONS

Lu et al, Chem. Soc. Rev., 2014, 43, 5561-5593.*

(Continued)

*Primary Examiner* — Clinton A Brooks
*Assistant Examiner* — Kofi Adzamli
(74) *Attorney, Agent, or Firm* — Gavrilovich, Dodd & Lindsey LLP

(57) ABSTRACT

The disclosure provides for metal organic frameworks (MOFs) that are selective adsorbents for aromatic hydrocarbons, devices comprising the MOFs thereof, and methods using the MOFS thereof for separating and/or storing aromatic hydrocarbons.

20 Claims, 11 Drawing Sheets

(56) References Cited

U.S. PATENT DOCUMENTS

| | | |
|---|---|---|
| 2003/0222023 A1 | 12/2003 | Mueller |
| 2004/0081611 A1 | 4/2004 | Muller |
| 2004/0225134 A1 | 11/2004 | Yaghi |
| 2004/0249189 A1 | 12/2004 | Mueller |
| 2004/0265670 A1 | 12/2004 | Muller |
| 2005/0004404 A1 | 1/2005 | Muller |
| 2005/0014371 A1 | 1/2005 | Tsapatsis |
| 2005/0124819 A1 | 6/2005 | Yaghi |
| 2005/0154222 A1 | 7/2005 | Muller |
| 2005/0192175 A1 | 9/2005 | Yaghi |
| 2006/0057057 A1 | 3/2006 | Muller |
| 2006/0135824 A1 | 6/2006 | Mueller |
| 2006/0154807 A1 | 7/2006 | Yaghi |
| 2006/0185388 A1 | 8/2006 | Muller |
| 2006/0252641 A1 | 11/2006 | Yaghi |
| 2006/0252972 A1 | 11/2006 | Pilliod |
| 2006/0287190 A1 | 12/2006 | Eddaoudi |
| 2007/0068389 A1 | 3/2007 | Yaghi |
| 2007/0202038 A1 | 8/2007 | Yaghi |
| 2007/0217982 A1 | 9/2007 | Wright |
| 2007/0248575 A1 | 10/2007 | Connor |
| 2008/0017036 A1 | 1/2008 | Schultink |
| 2008/0190289 A1 | 8/2008 | Muller |
| 2009/0155588 A1 | 6/2009 | Hesse |
| 2009/0183996 A1 | 7/2009 | Richter |
| 2009/0216059 A1 | 8/2009 | Reyes |
| 2009/0247654 A1 | 10/2009 | Rajendran |
| 2010/0069234 A1 | 3/2010 | Willis |
| 2010/0258004 A1* | 10/2010 | Matzger ............. B01D 53/02 95/96 |
| 2011/0015388 A1 | 1/2011 | Youngblood |
| 2011/0282067 A1 | 11/2011 | Li |
| 2011/0282071 A1 | 11/2011 | Shi |
| 2012/0028846 A1 | 2/2012 | Yaghi |
| 2012/0031268 A1 | 2/2012 | Yaghi |
| 2012/0130113 A1 | 5/2012 | Yaghi |
| 2012/0133939 A1 | 5/2012 | Yaghi |
| 2013/0047849 A1 | 2/2013 | Zhang |
| 2013/0096210 A1 | 4/2013 | Yaghi |
| 2014/0037944 A1 | 2/2014 | Dichtel |
| 2014/0148596 A1 | 5/2014 | Dichtel |

FOREIGN PATENT DOCUMENTS

| | | |
|---|---|---|
| DE | 102005023856 A1 | 11/2006 |
| DE | 102005054523 A1 | 5/2007 |
| EP | 1070538 A2 | 1/2001 |
| JP | 2007534658 A | 11/2007 |
| KR | 20100055350 A | 5/2010 |
| WO | 9905151 A | 2/1999 |
| WO | 2006110740 A2 | 10/2006 |
| WO | 2006122920 A1 | 11/2006 |
| WO | 2006125761 A2 | 11/2006 |
| WO | 2007007113 A2 | 1/2007 |
| WO | 2007118843 A1 | 10/2007 |
| WO | 2009073739 A1 | 6/2009 |
| WO | 2010056092 A2 | 5/2010 |
| WO | 2010080618 A2 | 7/2010 |
| WO | 2010083418 A1 | 7/2010 |
| WO | 2011127301 A2 | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Hupp et al., Angew. Chem. Int. Ed. 2014, 53, 4530-4540.*
Lu et al. (Chem. Soc. Rev, 43:5561-5593, 2014). (Year: 2014).*
Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.
Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.
Tanabe et al., 'Systematic Functionalization of a Metal-Organic Framework via a Postsynthetic Modification Approach,' J. Am. Chem. Soc. 130(26):8508-8517 (2008).
Tilford et al., 'Facile Synthesis of a Highly Crystalline, Covalently Porous Boronate Network,' 18(22):5296-5301 (Oct. 11, 2006).
Tranchemontagne et al., 'Hydrogen Storage in New Metal-Organic Frameworks,' J. Phys. Chem. C 116(24):13143-13151 (May 24, 2012).
Vitillo et al., 'Role of Exposed Metal Sites in Hydrogen Storage in MOFs,' J. Am. Chem. Soc. 130(26):8386-8396 (2008).
Wang, Zhenqiang, et al., 'Postsynthetic Covalent Modification of a Neutral Metal—Organic Framework', J. Am. Chem. Soc., (2007), vol. 129, No. 41, pp. 12368-12369.
Whitfield et al. Metal-organic frameworks based on iron oxide octahedral chains connected by benzendicarboxylate dianions. Solid State Sciences, 2005. vol. 7, pp. 1096-1103.
Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).
Yang et al., 'CH4 storage and C02 capture in highly porous zirconium oxide based metal-organic frameworks,' Chem. Commun., 48:9831-9833, Aug. 15, 2012.
Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).
Zhenqiang Wang et al., 'Tandem Modification of Metal-Organic Frameworks by a Postsynthetic Approach', Angew Chem Int Ed, (200800686), vol. 47, pp. 4699-4702.
Zhou et al., 'Introduction to Metal-Organic Frameworks,' Chemical Reviews 112:673-674 (Jan. 26, 2012).
Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.
Akporiaye et al., 'Combinatorial Approach to the Hydrothermal Synthesis of Zeolites,' Angew. Chemie 37(5):609-611 (1998).
Barman et al., 'Incorporation of active metal sites in MOFs via in situ generated ligand deficient metal-linker commplexes' Chem. Commun. 47:11882-11884 (Oct. 11, 2011).
Bhakta et al., 'Metal organic frameworks as templates for nanoscale NaAlH4', Journal of American Chemical Society, vol. 131, No. 37, Sep. 23, 2009, pp. S1-S14.
Britt et al., "Metal-Organic frameworks with high capacity and selectivity for harmful gases", PNAS, 2008, vol. 105, No. 33, pp. 11623-11627.
Burrows, Andrew D., 'Mixed-component metal-organic frameworks (MC-MOFs): enhancing functionality through solid solution formation and surface modifications', Crystengcomm, vol. 13, No. 11, Jan. 1, 2011, pp. 3623-3642.
Burrows, Andrew D., et al., "Post-Synthetic Modification of Tagged MOFs", Angewa. Chem. Int . Ed., (20081020), vol. 47, pp. 8482-8486, XP008150669.
Carboni et al., "Highly porous and stable metal-organic frameworks for uranium extraction," Chemical Science, 4:2396-2402, Apr. 4, 2013.
Carlucci et al., 'Nanoporous three-dimensional networks topologically related to cooperite from the self-assembly of copper(I)centres and 1,2,4,5-tetracyanobenzene,' New J. Chem. 23(23):397-401 (1999).
Chen et al. "Photoluminescent Metal-Organic Polymer Constructed from Trimetallic Clusters and Mixed Carboxylates", Inorg. Chem. 2003, 42, 944-946.

(56) References Cited

OTHER PUBLICATIONS

Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).
Chen, Binling, et. al., "Zeolitic imidazolate framework materials: recent progress in synthesis and applications", Journal of Materials Chemistry A: Materials for Energy and Sustainability, GB, (20140717), vol. 2, No. 40, doi:10.1039/C4TA02984D, ISSN 2050-7488, pp. 16811-16831, XP055337959.
Choi et al., 'Reversible Interpenetration in a Metal-Organic Framework Triggered by Ligand Removal and Addition,' Angew. Chem. Int. Ed. 51:8791-8795 (2012).
Chun et al., 'Concomitant Formation of N-Heterocyclic Carbene-Copper Comlexies within a Supramolecular Network in the Self-Assembly of Immidzolium Dicarboxylate with Metal Ions,' Inorganic Chemistry, Jul. 20, 2009, pp. 6353-6355, vol. 48, No. 14.
Chun et al., 'Cu2O: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Corma et al., 'A large-cavity zeolite with wide pore windows and potential as an oil refining catalyst,' Nature, vol. 418, pp. 514-517 (Aug. 2002).
Corma et al., "From MOFs to zeolites: zirconium sites for epoxide rearrangement," New J. of Chem. 37:3496-3502, Aug. 2, 2013.
Coskun et al., 'Metal-Organic Frameworks Incorporating Copper-Complexed Rotaxanes,' Angew. Chem. Int. Ed., 51:2160-2163 (2012).
Costa et al., 'Chemical Modification of a Bridging Ligand Inside a Metal-Organic Framework while Maintaining the 3D Structure,' Fur. J. Inorg. Chem. 10:1539-1545 (2008).
Cote et al., 'Porous, Crystalline, Covalent Organic Frameworks,' Science 310:1166-1170 (2005).
Cote et al., 'Reticular Synthesis of Microporous and Mesoporous 2D Covalent Organic Frameworks,' J. Am. Chem. Soc. 129:12914-12915 (2007).
Crees et al., 'Synthesis of a Zinc(II) Imidazolium Dicarboxylate Logand Metal-Organic Framework (MOF): a Potential Precursor to MOF-Tethered N-Heterocyclic Carbene Compounds,' Inorganic Chemistry, Jan. 19, 2010, vol. 49, No. 4, pp. 1712-1719.
Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).
Demessence, A et al., 'Strong CO2 Bnding in a Water-Stable, Triazolate-Bridged Metal-Organic Framework Functionalized with Ethylenediamine,' J. Am. Chem. Soc. 131:8784-8786 (2009).
Demir et al., 'Role of Copper Species in the Oxidative Dimerization of Arylboronic Acids: Synthesis of Symmetrical Biaryls,' Journal of Organic Chemistry 68(26):10130-10134 (2003).
Deng et al., 'Large-Pore Apertures in a Series of Metal-Organic Frameworks,' Science 336:1018-1023 (May 25, 2012).
Deng, H. et al., "Large-Pore Apertures in a Series of Metal-Organic Frameworks," Science, vol. 336, No. 6084, May 12, 2012, pp. 1018-1023.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC 2013, i, 66-100.
Dhakshinamoorthy et al., "Metal-organic frameworks as heterogeneous catalysts for oxidation reactions", Catal. Sci. Technol., Apr. 28, 2011, 1, 856-867.
Dietzel, Pascal D. C., et. al., "Application of metal-organic frameworks with coordinatively unsaturated metal sites in storage and separation of methane and carbon dioxide", Journal of Materials Chemistry, (20090821), vol. 19, No. 39, doi:10.1039/b911242a, ISSN 0959-9428, pp. 7362-7370, XP055197279.

Koh et al., 'A Crystalline Mesoporous Coordination Copolymer with High Microporosity,' Angew Chem Int'l, 2008, pp. 677-680, vol. 47.
Koh et al., "A Crystalline Mesoporous Coordination Copolymer with High Microporosity", Angew. Chem. Int. Ed. 2008, 120, pp. 689-692.
Kong et al., 'Mapping of Functional Groups in Metal-Organic Frameworks', Science, vol. 341, No. 6148, Jul. 25, 2013, pp. 882-885.
Koza et al., 'An efficient High Yielding Approach for the Homocoupling of Aryl Boronic Acids,' Synthesis 15:2183-2186 (2002).
Kyoungmoo et al., "A Crystalline Mesoporous Coordination Copolymer with High Microporosity," Angew. Chem. Int. Ed. 47(4):689-92 (2008).
Ling et al., 'A zinc(II) metal-organic framework based on triazole and dicarboxylate ligands for selective adsorption of hexane isomers,' Chem. Comm. 47:7197-7199 (2011).
Luo et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).
Mason, Jarad A., "Evaluating metal-organic frameworks for natural gas storage", Chemical Science, vol. 5, Accepted Oct. 22, 2013, pp. 32-51.
McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.
Mendoza-Cortes et al., 'Adsorption Mechanism and Uptake of Methane in Covalent Organic Frameworks: Theory and Experiment,' J. Phys. Chem. 114:10824-10833 (2010).
Morris et al., 'Framework mobility in the metal-organic framework crystal IRMOF-3: Evidence for aromatic ring and amine rotation,' Journal of Molecular Structure 1004:94-101 (2011).
Morris et al., 'Synthesis, Structure, and Metalation of Two New Highly Porous Zirconium Metal-Organic Frameworks,' Inorg. Chem. 51:6443-6445 (Jun. 7, 2012).
O'Keeffe et al., 'Deconstructing the Crystal Structures of Metal-Organic Frameworks and Related Materials into Their Underlying Nets,' Chem. Rev. 112(2):675-702 (Feb. 8, 2012).
Oisaki et al., "A Metal-Organic Framework with Covalently Bound Organometallic Complexes," J. of the Amer. Chem. Soc., pp. 9262-9264, vol. 132, No. 27, 2010.
Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.
Dugan et al., 'Covalent modification of a metal-organic framework with isocyanates: probing substrate scope and reactivity,' 29:3366-3368 (2008).
Eddaoudi, M et al., "Systematic Design of Pore Size and Functionality in Isoreticular MOFs and Their application in Methane Storage" Science, (2002), vol. 295, pp. 469-472.
Forster et al., 'A High-Throughput Investigation of the Role of pH, Temperature, Concentration, and Time on the Synthesis of Hybrid Inorganic-Organic Materials,' Angew. Chemie Int. Ed. 44(46):7608-7611 (2005).
Fracaroli et al., 'Isomers of Metal-Organic Complex Arrays,' Inorg. Chem. 51: 6437-6439 (Jun. 5, 2012).
Fracaroli, A.M. et al., Metal-Organic Frameworks with Precisely Designed Interior for Carbon Dioxide Capture in the Presence of Water, J. Am. Chem. Soc, Jun. 25, 2014, vol. 136, No. 25, pp. 8863-8866.
Furukawa et al., 'Isoreticular Expansion of MetalOrganic Frameworks with Triangular and Square Building Units and the Lowest Calculated Density for Porous Crystals,' Inorg. Chem. 50:9147-9152 (2011).
Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).

(56) References Cited

OTHER PUBLICATIONS

Furukawa et al., "Water Adsorption in Porous Metal-Organic Frameworks and Related Materials," J. of the Amer. Chem. Soc, vol. 136, No. 11, pp. 4369-4381, Published: Mar. 3, 2014.

Gadzikwa, T. et al., 'Selective Bifunctional Modification of a Non-catenated Metal-Organic Framework Material via Click Chemistry,' J. Am. Chem. Soc. 131:13613-13615 (2009).

Galli et al., 'Adsorption of Harmful Organic Vapors by Flexible Hydrophobic Bis-pyrazolate Based MOFs,' Chem. Mater. 22(5):1664-1672 (2010).

Gandara et al., 'High Methane Storage Capacity in Aluminum Metal-Organic Frameworks', Journal of the American Chemical Society, vol. 136, No. 14, Mar. 21, 2014, pp. 5271-5274.

Gandara et al., 'Porous, Conductive Metal-Triazolates and Their Structural Elucidation by the Charge-Flipping Method,' Chem. Eur. J. 18:10595-10601 (2012).

Gandara, Felipe, et al., "Crystallography of metal-organic frameworks", IUCRJ, vol. 1, No. 6, Oct. 28, 2014, pp. 563-570.

Garibay et al., "Isoreticular synthesis and modification of frameworks with the UiO-66 topology," Chemical Communications, 46:7700-7702, Sep. 27, 2010.

Gassensmith et al., 'Strong and Reversible Binding of Carbon Dioxide in a Green Metal-Organic Framework,' J. Am. Chem. Soc. 133:15312-15315 (Aug. 30, 2011).

Gonzalez-Arellano et al., 'Homogeneous and heterogeneous Au(III) Schiff base-complexes as selective and general catalysts for self-coupling of aryl boronic acids,' Chem. Comm. 15:1990-1992 (2005).

Goto, Y et al., "Clickable Metal-Organic Framework," J. Am. Chem. Soc. 130:14354-14355 (2008).

Han et al., 'Covalent Organic Frameworks as Exceptional Hydrogen Storage Materials,' J. Am. Chem. Soc. 130:11580-11581 (2008).

Kirai et al., 'Homocoupling of arylboronic acids catalyzed by 1,10-phenanthroline-ligated copper complexes in air,' European Journal of Organic Chemistry 12:1864-1867 (2009).

\* cited by examiner

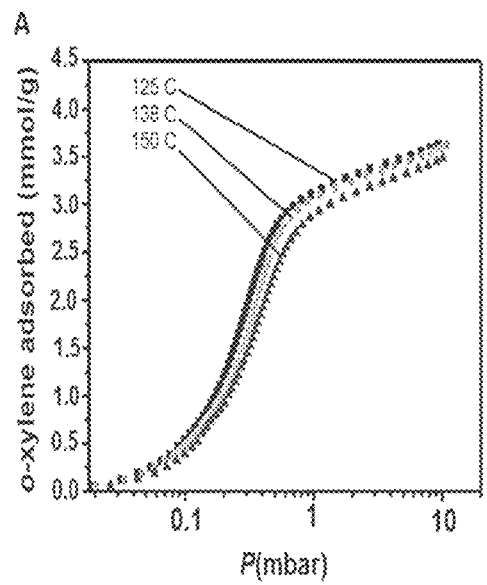
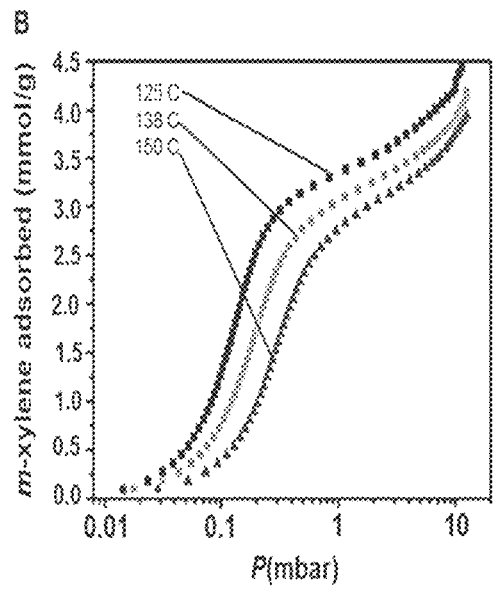
FIG. 1A          FIG. 1B
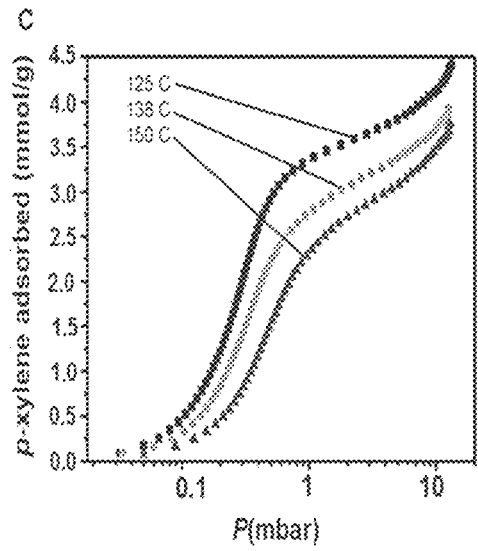
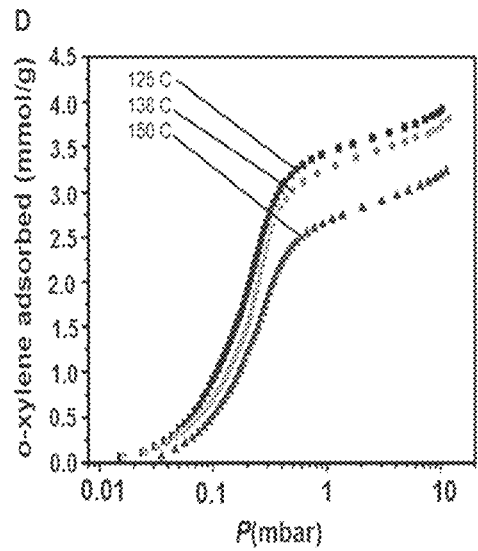
FIG. 1C          FIG. 1D

FIG. 3A-C

METAL-ORGANIC FRAMEWORKS FOR AROMATIC HYDROCARBON SEPARATIONS

CROSS REFERENCE TO RELATED APPLICATIONS

This application claims priority under 35 U.S.C. § 119 from Provisional Application Ser. No. 62/087,201, filed Dec. 3, 2014, the disclosure of which is incorporated herein by reference.

STATEMENT REGARDING FEDERALLY SPONOSRED RESEARCH

This invention was made with government support under Grant Number DE-SC0001015 awarded by the Department of Energy. The government has certain rights in the invention.

TECHNICAL FIELD

The disclosure provides for metal-organic frameworks (MOFs), and the use of the MOFs as porous adsorbents for the adsorptive separation of aromatic hydrocarbons.

BACKGROUND

Metal-organic frameworks (MOFs) are porous crystalline materials that are constructed by linking metal clusters called Secondary Building Units (SBUs) and organic linking ligands. MOFs have high surface area and high porosity, which enable them to be utilized in diverse fields such as gas storage, catalysis, and sensors.

SUMMARY

The disclosure provides for metal-organic frameworks (MOFs) that can be used as porous adsorbents for the adsorptive separation of aromatic hydrocarbons. The hydrocarbons of interest include, but are not limited to, benzene, toluene, ethylbenzene, and the three xylene isomers (ortho, meta, para). The fine tuning of the pore shape and geometry of a specific class of metal-organic frameworks, materials containing coordinatively-unsaturated metal cation sites, can be utilized to prepare materials with specific metal-metal separation distances which engender these materials with cooperative, multi-site adsorption behavior. Due to their high surface areas, thermal stabilities, and tunable nature, these MOFs are ideal for use in large scale processing plants and represent a tremendous improvement over current adsorptive based separation materials. Three specific MOFs tested herein display varying metal-metal separation distances, allowing for the fine tuning of the metal-metal separation distances. The MOFs were used as an adsorbent that was able to separate a four component mixture containing ethylbenzne, meta-xylene, ortho-xylene, and para-xylene into pure components. Accordingly, the MOFs of the type specified in this disclosure are ideally suited for the separation of aromatic hydrocarbon streams into pure or enriched component streams from petroleum refinery naphthas and pyrolysis gasoline in industrial hydrocarbon production via temperature and/or pressure swing adsorption in the gas or liquid phase.

In a particular embodiment, the disclosure provides for a metal-organic framework (MOF) comprising a repeating core having the general structure M-L-M, wherein M is a metal or metal ion, and L is a linking moiety comprising a structure of Formula I, II and/or Formula III:

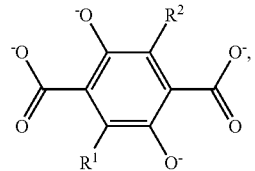

Formula (I)

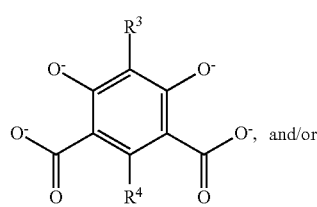

Formula (II)

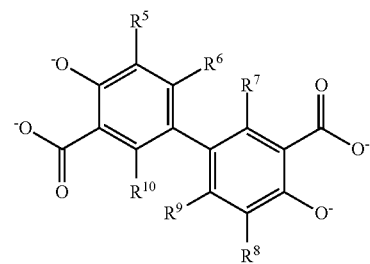

Formula (III)

wherein, $R^1$-$R^{10}$ are independently selected from H, D, FG, optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$)cycloalkyl, optionally substituted ($C_1$-$C_{12}$)cycloalkenyl, optionally substituted aryl, optionally substituted heterocycle, optionally substituted mixed ring system, —C($R^{11}$)$_3$, —CH($R^{11}$)$_2$, —CH$_2$$R^{11}$, —C($R^{12}$)$_3$, —CH($R^{12}$)$_2$, —CH$_2$$R^{12}$, —OC($R^{11}$)$_3$, OCH($R^{11}$)$_2$, —OCH$_2$$R^{11}$, —OC($R^{12}$)$_3$, —OCH($R^{12}$)$_2$, OCH$_2$$R^{12}$; $R^{11}$ is selected from FG, optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, hemiacetal, hemiketal, acetal, ketal, and orthoester, F, Cl, Br, I; and $R^{12}$ is selected from one or more substituted or unsubstituted rings selected from cycloalkyl, aryl and heterocycle; wherein the MOF comprises coordinatively-unsaturated metal cation sites, and wherein the MOF is a selective adsorbent for aromatic hydrocarbons by having multiple unsaturated metal cation sites that can come into contact with an aromatic hydrocarbon to form multiple metal site-hydrocarbon molecule interactions.

In another embodiment, the disclosure provides for a MOF comprising a repeating core having the general structure M-L-M, wherein M is a metal or metal ion, and L is a linking moiety comprising a structure of Formula I, II and/or Formula III:

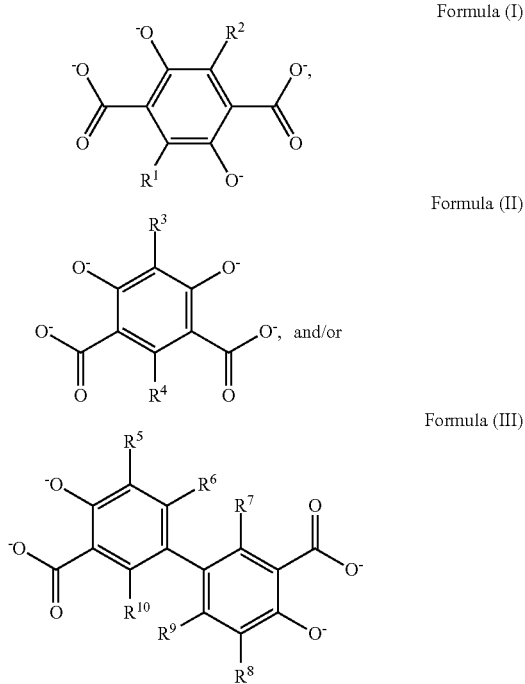

Formula (I)

Formula (II)

Formula (III)

wherein, $R^1$-$R^{10}$ are independently selected from H, halo, amino, amide, imine, azide, methyl, cyano, nitro, nitroso, hydroxyl, aldehyde, carbonyl, ester, thiol, sulfinyl, sulfonyl, and thiocyanate.

In a yet further embodiment, the MOF disclosed herein comprises one or more metals or metal ions selected from: $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Ta^{4+}$, $Ta^{3+}$, $Tm^{2+}$, $Yb^{3+}$, $Yb^{2+}$, $Lu^{3+}$, $La^{3+}$, $La^{2+}$, $La^+$, and combinations thereof, including any complexes which contain the metals or metal ions, as well as any corresponding metal salt counter-anions. In another embodiment, the MOFs disclosed herein comprise one or more divalent metal ions selected from: $Be^{2+}$, $Mg^{2+}$, $Ca^{2+}$, $Sr^{2+}$, $Ba^{2+}$, $Sc^{2+}$, $Y^{2+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $Db^{2+}$, $Tm^{2+}$, $Yb^{2+}$, and $La^{2+}$, including any complexes which contain the metal ions, as well as any corresponding metal salt counter-anions. In a particular embodiment, the MOF disclosed herein comprise $Co^{2+}$.

In yet another embodiment, the disclosure provides for a MOF that comprises a repeating core of $Co_2$(dobdc), $Co_2$(m-dobdc) or $Co_2$(dobpdc) ($dobdc^{4-}$=2,5-dioxido-1,4-benzenedicarboxylate, $m-dobdc^{4-}$=4,6-dioxido-1,3-benzenedicarboxylate, $dobpdc^{4-}$=4,4'-dioxido-3,3'-biphenyldicarboxylate).

In a particular embodiment, the disclosure provides for a MOF where two neighboring metals have open coordination sites oriented in a way such that they can both be contacted by an aromatic hydrocarbon. In another embodiment, the disclosure provides for a MOF where the metal-metal separation distance of the MOF is from about 7.0 Å to about 12.7 Å. In yet another embodiment, the disclosure provides for a MOF that comprises 1-D hexagonal channels with a high density of 5-coordinate metal centers with a sixth, vacant coordination site pointing into the pores.

In a certain embodiment, a MOF disclosed herein is reacted with a post framework reactant that adds at least one effect to a MOF selected from: modulating the aromatic hydrocarbon storage and/or separation ability of the MOF; modulating the sorption properties of the MOF; modulating the pore size of the MOF; and modulating the metal-metal separation distance of the MOF.

In a particular embodiment, the disclosure provides for a device that comprises a MOF of the disclosure. In a further embodiment, the device is an aromatic hydrocarbon separation and/or aromatic hydrocarbon storage device. In yet a further embodiment, the device comprises a MOF of the disclosure as an aromatic hydrocarbon adsorbent. In another embodiment, the device is used in a catalytic reforming process, or with reformates generated from a catalytic reforming process. In yet another embodiment, the device is used to separate a multicomponent aromatic hydrocarbon stream into pure or enriched single component aromatic stream.

In a certain embodiment, the disclosure provides for a method of separating and/or storing one or more aromatic hydrocarbons from a mixture comprising aromatic hydrocarbons comprising contacting the mixture with a MOF of the disclosure. In a further embodiment, the mixture comprises reformates from a catalytic reforming process. In another embodiment, the mixture comprises aromatic hydrocarbons selected from toluene, ethylbenzene, benzene, para-xylene, meta-xylene, ortho-xylene, durene, mesitylene, biphenyl, naphthalene, anthracene, phenanthrene, and any combination thereof. In a particular embodiment, the mixture comprises aromatic hydrocarbons selected from ethylbenzene, para-xylene, meta-xylene, and ortho-xylene.

DESCRIPTION OF DRAWINGS

FIG. 1A-F shows single-component isotherms in $Co_2$(dobdc) and $Co_2$(m-dobdc). Isotherms measured on vapor phase xylenes at 125, 138, and 150° C. A, o-xylene, B, m-xylene, and C, p-xylene isotherms in $Co_2$(dobdc). D, o-xylene, E, m-xylene, and F, p-xylene isotherms in $Co_2$(m-dobdc).

FIG. 3A-C shows in situ single-crystal x-ray diffraction structures in $Co_2(dobdc)$. The structures of (A), m xylene, (B), ethylbenzene, and (C), o-xylene in $Co_2(dobdc)$ showing the interaction of a single xylene molecule with two metal centers. The different strengths of adsorption of these isomers stem from the shape of each isomer and the ability of it to fit in the pocket across the ligand between two Co(II) centers.

DETAILED DESCRIPTION

Figure 1E:
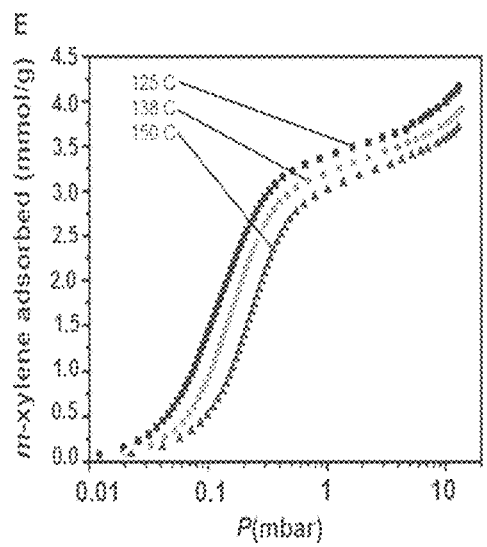

As used herein and in the appended claims, the singular forms "a," "an," and "the" include plural referents unless the context clearly dictates otherwise. Thus, for example, reference to "an organic linking ligand" includes a plurality of such linking ligands and reference to "the metal ion" includes reference to one or more metal ions and equivalents thereof known to those skilled in the art, and so forth.

Unless defined otherwise, all technical and scientific terms used herein have the same meaning as commonly understood to one of ordinary skill in the art. Although there are many methods and reagents similar or equivalent to those described herein, the exemplary methods and materials are presented herein.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cycloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "framework" as used herein, refers to a highly ordered structure comprised of secondary building units (SBUs) that can be linked together in defined, repeated and controllable manner, such that the resulting structure is characterized as being porous, periodic and crystalline. Typically, "frameworks" are two dimensional (2D) or three dimensional (3D) structures. Examples of "frameworks" include, but are not limited to, "metal-organic frameworks" or "MOFs", "zeolitic imidazolate frameworks" or "ZIFs", or "covalent organic frameworks" or "COFs". While MOFs and ZIFs comprise SBUs of metals or metal ions linked together by forming covalent bonds with linking clusters on organic linking moieties, COFs are comprised of SBUs of organic linking moieties that are linked together by forming covalent bonds via linking clusters. As used herein, "framework" does not refer to coordination complexes or metal complexes. Coordination complexes or metal complexes are comprised of a relatively few number of centrally coordinated metal ions (i.e., less than 4 central ions) that are coordinately bonded to molecules or ions, also known as ligands or complexing agents. By contrast, "frameworks" are highly ordered and extended structures that are not based upon a centrally coordinated ion, but involve many repeated secondary building units (SBUs) linked together (e.g., >10, >100, >1000, >10,000, etc). Accordingly, "frameworks" are orders of magnitude much larger than coordination complexes and have different structural and chemical properties due to the framework's open and ordered structure.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FGs that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls. In a particular embodiment, the hydrocarbon is an aromatic hydrocarbon.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "unsubstituted" with respect to hydrocarbons, heterocycles, and the like, refers to structures wherein the parent chain contains no substituents.

Aromatic compound of the formula $C_8H_{10}$, including ethylbenzene and meta-, ortho-, and para-xylene are important chemical commodities with annual production in excess of 39 Mt. The separation of these isomers takes place within the so called "aromatic complex" which consists of a number of processes that are used to convert reformates and pyrolysis gasoline into the basic chemical feedstocks benzene, toluene, and xylenes (BTX). This process is typically done in three steps. First catalytic reforming converts petroleum refinery naphthas into products called reformates which contain a large amount of aromatics, the components of high-octane gasoline. These reformates are then fed to a second step. Alternatively, pyrolysis gasoline, a by-product of the steam cracking of hydrocarbons in the production of ethylene, is used. During the second part of the aromatic complex three different aromatic streams are produced: pure benzene, pure toluene, and mixed xylenes. The majority of mixed xylenes, which are typically present at 20% ortho-, 42% meta-, 18% para-, and 20% ethylbenzene, are processed further to produce one or more of the pure isomers. As the natural mixed product stream does not match market demand for each individual isomer, the stream is processed through the commonly referred to "$C_8$-aromatics loop". This process first separates the desired isomers (mainly para and some ortho) then sends the feed to an isomerization unit, which brings the isomers back to their thermodynamic equilibrium. Of the 39.2 Mt of xylenes produced in 2008, 33.0 Mt was used as pure para, 3.6 Mt as ortho, 0.4 Mt as meta, with the rest used directly without separation as "mixed xylenes" solvent.

To fulfill the large need for pure para-xylene there is tremendous importance placed on the separation of the mixed xylenes stream. It is basically impossible to obtain pure xylene via distillation as the boiling points of the four components are essentially identical. Current state-of-the-art technology involves either crystallization or adsorption for separation, with about 25% of the worldwide production using the former and 75% the latter. All present adsorption-based techniques for the production of pure para-xylene are carried out in the liquid phase using moving bed technology with typical xylene purity and recovery of 99.7-99.9% and 97-99%, respectively. Ortho-xylene can often be separated by fractional distillation as its boiling point is about 5° C. higher than the other isomers. Other adsorption and complexation based processes are often used to obtain the other isomers. However, there are few processes that utilize a single adsorbent for the separation of all four $C_8$ isomers.

Metal-organic frameworks (MOFs) are porous crystalline materials that are constructed by the linkage of inorganic metal clusters called secondary building units (SBUs) with organic linkers. These materials have very large surface areas and pore volumes. Therefore, MOFs are ideally suited for use in gas sorption and/or gas separation. For a possible commercialization of a MOF adsorbent, it must meet several criteria including low cost components, high stability and high gas sorption performance. MOFs have been shown to have tremendous utility in the separation of various hydrocarbon mixtures, including ethane/ethylene, propane/propylene, and $C_5$ alkane mixtures, among many others.

The disclosure demonstrates the unanticipated interaction of a single xylene molecule with two coordinatively unsaturated metal centers in the metal-organic frameworks $Co_2$(dobdc) and $Co_2$(m-dobdc). This interaction was shown to effect the separation of the $C_8$ aromatics based on small differences in how these guests interact with the metal-organic framework surface. Furthermore, unexpected flexibility of the $Co_2$(dobdc) framework endows this material with exceptional xylene separation properties.

The disclosure provides for the preparation of metal-organic frameworks containing a high-density of coordinatively-unsaturated metal cation sites which have the correct pore geometry and metal site arrangement to allow for a single hydrocarbon molecule, such as a xylene isomer, to interact with multiple metal sites at the same time. The MOFs of the disclosure therefore have high selectivities for adsorbing and separating structurally related hydrocarbons (e.g., isomers) due to these multiple metal site-hydrocarbon molecule interactions that heretofore has not been previously shown. Accordingly, molecules with very similar physical properties (e.g., melting points, boiling points, kinetic diameters, and shape) can now be separated based on differences in how they interact with the metal-organic framework surface.

In a particular embodiment, the disclosure provides for MOFs that have high selectivities for aromatic hydrocarbons comprising a repeating core having the general structure M-L-M, wherein M is transition metal or metal ion, and wherein L is a linking moiety comprising a structure of Formula I, II and/or Formula III:

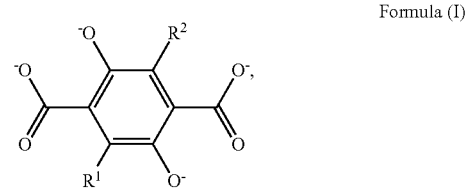

Formula (I)

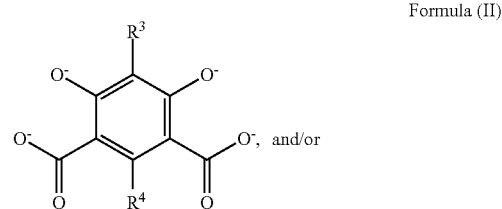

Formula (II)

and/or

Formula (III)

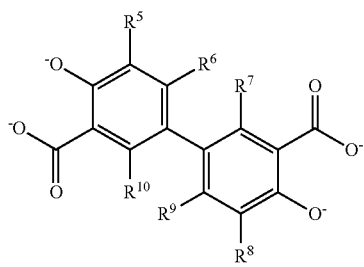

wherein,

R$^1$-R$^{10}$ are independently selected from H, D, FG, optionally substituted (C$_1$-C$_{12}$)alkyl, optionally substituted hetero-(C$_1$-C$_{12}$)alkyl, optionally substituted (C$_1$-C$_{12}$)alkenyl, optionally substituted hetero-(C$_1$-C$_{12}$)alkenyl, optionally substituted (C$_1$-C$_{12}$)alkynyl, optionally substituted hetero-(C$_1$-C$_{12}$)alkynyl, optionally substituted (C$_1$-C$_{12}$)cycloalkyl, optionally substituted (C$_1$-C$_{12}$)cycloalkenyl, optionally substituted aryl, optionally substituted heterocycle, optionally substituted mixed ring system, —C(R$^{11}$)$_3$, —CH(R$^{11}$)$_2$, —CH$_2$R$^{11}$, —C(R$^{12}$)$_3$, —CH(R$^{12}$)$_2$, —CH$_2$R$^{12}$, —OC(R$^{11}$)$_3$, OCH(R$^{11}$)$_2$, —OCH$_2$R$^{11}$, —OC(R$^{12}$)$_3$, —OCH(R$^{12}$)$_2$, OCH$_2$R$^{12}$;

R$^{11}$ is selected from FG, optionally substituted (C$_1$-C$_{12}$) alkyl, optionally substituted hetero-(C$_1$-C$_{12}$)alkyl, optionally substituted (C$_1$-C$_{12}$)alkenyl, optionally substituted hetero-(C$_1$-C$_{12}$)alkenyl, optionally substituted (C$_1$-C$_{12}$) alkynyl, optionally substituted hetero-(C$_1$-C$_{12}$)alkynyl, hemiacetal, hemiketal, acetal, ketal, and orthoester; and R$^{12}$ is selected from one or more substituted or unsubstituted rings selected from cycloalkyl, aryl and heterocycle.

In a further embodiment, the disclosure provides for MOFs that have high selectivities for aromatic hydrocarbons comprising a repeating core having the general structure M-L-M, wherein M is a transition metal or metal ion, and L is a linking moiety comprising a structure of Formula I, II and/or Formula III:

Formula (I)

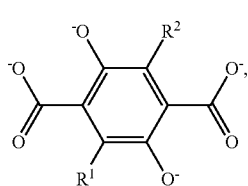

Formula (II)

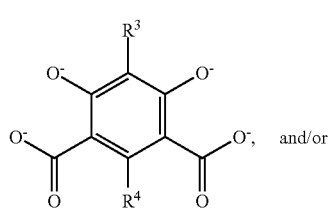

and/or

Formula (III)

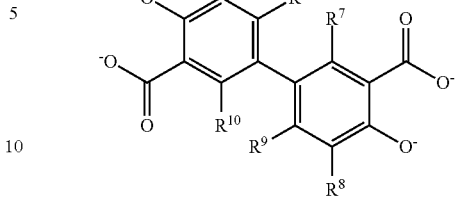

wherein,

R$^1$-R$^{10}$ are independently selected from H, halo, amino, amide, imine, azide, methyl, cyano, nitro, nitroso, hydroxyl, aldehyde, carbonyl, ester, thiol, sulfinyl, sulfonyl, and thiocyanate.

In a particular embodiment, the disclosure provides for a MOF which comprises one or more metals or metal ions selected from: Li$^+$, Na$^+$, K$^+$, Rb$^+$, Cs$^+$, Be$^{2+}$, Mg$^{2+}$, Ca$^{2+}$, Sr$^{2+}$, Ba$^{2+}$, Sc$^{3+}$, Sc$^{2+}$, Sc$^+$, Y$^{3+}$, Y$^{2+}$, Y$^+$, T$^{4+}$, Ti$^{3+}$, Ti$^{2+}$, Zr$^{4+}$, Zr$^{3+}$, Zr$^{2+}$, Hf$^{4+}$, Hf$^{3+}$, V$^{5+}$, V$^{4+}$, V$^{3+}$, V$^{2+}$, Nb$^{5+}$, Nb$^{4+}$, Nb$^{3+}$, Nb$^{2+}$, Ta$^{5+}$, Ta$^{4+}$, Ta$^{3+}$, Ta$^{2+}$, Cr$^{6+}$, Cr$^{5+}$, Cr$^{4+}$, Cr$^{3+}$, Cr$^{2+}$, Cr$^+$, Cr, Mo$^{6+}$, Mo$^{5+}$, Mo$^{4+}$, Mo$^{3+}$, Mo$^{2+}$, Mo$^+$, Mo, W$^{6+}$, W$^{5+}$, W$^{4+}$, W$^{3+}$, W$^{2+}$, W$^+$, W, Mn$^{7+}$, Mn$^{6+}$, Mn$^{5+}$, Mn$^{4+}$, Mn$^{3+}$, Mn$^{2+}$, Mn$^+$, Re$^{7+}$, Re$^{6+}$, Re$^{5+}$, Re$^{4+}$, Re$^{3+}$, Re$^{2+}$, Re$^+$, Re, Fe$^{6+}$, Fe$^{4+}$, Fe$^{3+}$, Fe$^{2+}$, Fe$^+$, Fe, Ru$^{8+}$, Ru$^{7+}$, Ru$^{6+}$, Ru$^{4+}$, Ru$^{3+}$, Ru$^{2+}$, Os$^{8+}$, Os$^{7+}$, Os$^{6+}$, Os$^{5+}$, Os$^{4+}$, Os$^{3+}$, Os$^{2+}$, Os$^+$, Os, Co$^{5+}$, Co$^{4+}$, Co$^{3+}$, Co$^{2+}$, Co$^+$, Rh$^{6+}$, Rh$^{5+}$, Rh$^{4+}$, Rh$^{3+}$, Rh$^{2+}$, Rh$^+$, Ir$^{6+}$, Ir$^{5+}$, Ir$^{4+}$, Ir$^{3+}$, Ir$^{2+}$, Ir$^+$, Ir, Ni$^{3+}$, Ni$^{2+}$, Ni$^+$, Ni, Pd$^{6+}$, Pd$^{4+}$, Pd$^{2+}$, Pd$^+$, Pd, Pt$^{6+}$, Pt$^{5+}$, Pt$^{4+}$, Pt$^{3+}$, Pt$^{2+}$, Pt$^+$, Cu$^{4+}$, Cu$^{3+}$, Cu$^{2+}$, Cu$^+$, Ag$^{3+}$, Ag$^{2+}$, Ag$^+$, Au$^{5+}$, Au$^{4+}$, Au$^{3+}$, Au$^{2+}$, Au$^+$, Zn$^{2+}$, Zn$^+$, Zn, Cd$^{2+}$, Cd$^+$, Hg$^{4+}$, Hg$^{2+}$, Hg$^+$, B$^{3+}$, B$^{2+}$, B+, Al$^{3+}$, Al$^{2+}$, Al$^+$, Ga$^{3+}$, Ga$^{2+}$, Ga$^+$, In$^{3+}$, In$^{2+}$, In$^{1+}$, Tl$^{3+}$, Tl$^+$, Si$^{4+}$, Si$^{3+}$, Si$^{2+}$, Si$^+$, Ge$^{4+}$, Ge$^{3+}$, Ge$^{2+}$, Ge$^+$, Ge, Sn$^{4+}$, Sn$^{2+}$, Pb$^{4+}$, Pb$^{2+}$, As$^{5+}$, As$^{3+}$, As$^{2+}$, As$^+$, Sb$^{5+}$, Sb$^{3+}$, Bi$^{5+}$, Bi$^{3+}$, Te$^{6+}$, Te$^{5+}$, Te$^{4+}$, Te$^{2+}$, La$^{3+}$, La$^{2+}$, Ce$^{4+}$, Ce$^{3+}$, Ce$^{2+}$, Pr$^{4+}$, Pr$^{3+}$, Pr$^{2+}$, Nd$^{3+}$, Nd$^{2+}$, Sm$^{3+}$, Sm$^{2+}$, Eu$^{3+}$, Eu$^{2+}$, Gd$^{3+}$, Gd$^{2+}$, Gd$^+$, Tb$^{4+}$, Tb$^{3+}$, Tb$^{2+}$, Tb$^+$, Db$^{3+}$, Db$^{2+}$, Ho$^{3+}$, Er$^{3+}$, Tm$^{4+}$, Tm$^{3+}$, Tm$^{2+}$, Yb$^{3+}$, Yb$^{2+}$, Lu$^{3+}$, La$^{3+}$, La$^{2+}$, La$^+$, and combinations thereof, including any complexes which contain the metals or metal ions, as well as any corresponding metal salt counter-anions. In another embodiment, the MOFs disclosed herein comprise one or more divalent metal ions selected from: Be$^{2+}$, Mg$^{2+}$, Ca$^{2+}$, Sr$^{2+}$, Ba$^{2+}$, Sc$^{2+}$, Y$^{2+}$, Ti$^{2+}$, Zr$^{2+}$, V$^{2+}$, Nb$^{2+}$, Ta$^{2+}$, Cr$^{2+}$, Mo$^{2+}$, W$^{2+}$, Mn$^{2+}$, Re$^{2+}$, Fe$^{2+}$, Ru$^{2+}$, Os$^{2+}$, Co$^{2+}$, Rh$^{2+}$, Ir$^{2+}$, Ni$^{2+}$, Pd$^{2+}$, Pt$^{2+}$, Cu$^{2+}$, Ag$^{2+}$, Au$^{2+}$, Zn$^{2+}$, Cd$^{2+}$, Hg$^{2+}$, B$^{2+}$, Al$^{2+}$, Ga$^{2+}$, In$^{2+}$, Si$^{2+}$, Ge$^{2+}$, Sn$^{2+}$, Pb$^{2+}$, As$^{2+}$, Te$^{2+}$, La$^{2+}$, Ce$^{2+}$, Pr$^{2+}$, Nd$^{2+}$, Sm$^{2+}$, Eu$^{2+}$, Gd$^{2+}$, Tb$^{2+}$, Db$^{2+}$, Tm$^{2+}$, Yb$^{2+}$, and La$^{2+}$, including any complexes which contain the metal ions, as well as any corresponding metal salt counter-anions. In a particular embodiment, the MOF disclosed herein comprise Co$^{2+}$.

In another embodiment, the disclosure provides for MOFs that have high selectivities for aromatic hydrocarbons comprising repeating cores of Co$_2$(dobdc), Co$_2$(m-dobdc), and/or Co$_2$(dobpdc) (dobdc$^{4-}$=2,5-dioxido-1,4-benzenedicarboxylate, m-dobdc$^{4-}$=4,6-dioxido-1,3-benzenedicarboxylate, dobpdc$^{4-}$=4,4'-dioxido-3,3'-biphenyldicarboxylate). The metal-metal distance across the ligand on the pore wall ranges from approximately 7.0 Å in the case of Co$_2$(m-dobdc) to 12.7 Å in Co$_2$(dobpdc). The metal-metal distance of 8.0 Å in Co$_2$(dobdc), coupled with unexpected framework flexibility, endow this material with exceptional xylene separation properties.

In a further embodiment a MOF disclosed herein comprises 1-D hexagonal channels. In yet a further embodiment, A MOF of the disclosure comprises a high density of 5-coordinate cobalt(II) centers with an open coordination site pointing into the channels within the framework.

All the aforementioned linking ligands possess appropriate reactive functionalities can be chemically transformed by a suitable reactant post synthesis of the framework to add further functionalities to the framework. By modifying the organic links within the framework post-synthetically, access to functional groups that were previously inaccessible or accessible only through great difficulty and/or cost is possible and facile.

In a further embodiment, the MOFs of the disclosure may be further modified by reacting with one or more post framework reactants that may or may not have denticity. In another embodiment, a MOF as-synthesized is reacted with at least one, at least two, or at least three post framework reactants. In yet another embodiment, a MOF as-synthesized is reacted with at least two post framework reactants. In a further embodiment, a MOF as-synthesized is reacted with at least one post framework reactant that will result in adding denticity to the framework.

The disclosure provides that a MOF disclosed herein can be modified by a post framework reactant by using chemical reactions that modify, substitute, or eliminate a functional group post-synthesis. These chemical reactions may use one or more similar or divergent chemical reaction mechanisms depending on the type of functional group and/or post framework reactant used in the reaction. Examples of chemical reaction include, but are not limited to, radical-based, unimolecular nucleophilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericyclic, electrocyclic, rearrangement, carbene, carbenoid, cross coupling, and degradation. Other agents can be added to increase the rate of the reactions disclosed herein, including adding catalysts, bases, and acids.

In another embodiment, a post framework reactant adds at least one effect to a MOF of the disclosure including, but not limited to, modulating the aromatic hydrocarbon storage and/or separation ability of the MOF; modulating the sorption properties of the MOF; modulating the pore size of the MOF; modulating the catalytic activity of the MOF; modulating the conductivity of the MOF; modulating the metal-metal separation distance of the MOF; and modulating the sensitivity of the MOF to the presence of an analyte of interest. In a further embodiment, a post framework reactant adds at least two effects to the MOF of the disclosure including, but not limited to, modulating the aromatic hydrocarbon storage and/or separation ability of the MOF; modulating the sorption properties of the MOF; modulating the pore size of the MOF; modulating the catalytic activity of the MOF; modulating the conductivity of the MOF; modulating the metal-metal separation distance of the MOF; and modulating the sensitivity of the MOF to the presence of an analyte of interest.

In one embodiment, a post framework reactant can be a saturated or unsaturated heterocycle.

In another embodiment, a post framework reactant has 1-20 carbons with functional groups including atoms such as N, S, and O.

In yet another embodiment, a post framework reactant is selected to modulate the size of the pores of a MOF disclosed herein.

In another embodiment, a post framework reactant is selected to increase the specificity of a MOF disclosed herein to a particular aromatic hydrocarbon.

In yet another embodiment, a post framework reactant is selected to modulate the aromatic hydrocarbon separation ability of a MOF disclosed herein.

In a further embodiment, a post framework reactant is selected to modulate the aromatic hydrocarbon sorption properties of a MOF of the disclosure. In another embodiment, a post framework reactant is selected to promote or increase aromatic hydrocarbon sorption of a MOF disclosed herein.

In yet a further embodiment, a post framework reactant is selected to increase or add catalytic efficiency to a MOF disclosed herein.

In another embodiment, a post framework reactant is selected so that organometallic complexes can be tethered to a MOF of the disclosure. Such tethered organometallic complexes can be used, for example, as heterogeneous catalysts.

Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase. The MOFs of the disclosure can therefore be used as selective adsorbents for aromatic hydrocarbons. Furthermore, the MOFs of the disclosure can be used to separate a mixture of aromatic hydrocarbons.

In particular embodiment, the disclosure provides for MOFs that can be tuned to adsorb a specific aromatic hydrocarbon or multiple aromatic hydrocarbons from a mixture comprising one or more aromatic hydrocarbons. For example, a MOF disclosed herein that is comprised of different types of linking ligands can provide adsorption sites that have differential binding/interaction characteristics for specific aromatic hydrocarbon molecules.

In one embodiment of the disclosure, an aromatic hydrocarbon storage or aromatic hydrocarbon separation material comprising one or more MOFs of the disclosure is provided. Advantageously, the MOFs of the disclosure include a number of adsorption sites for storing and/or separating aromatic hydrocarbons. Suitable examples of such aromatic hydrocarbons include, but are not limited to, aromatic hydrocarbons comprising xylene, toluene, benzene, ethylbenzene, mesitylene, durene, 2-phenylhexane, biphenyl, phenol, aniline, nitrobenzene, benzoic acid, naphthalene, anthracene, phenanthrene, and combinations thereof. Additionally, the MOFs of the disclosure have high selectivities for adsorbing aromatic hydrocarbons and are able to separate and/or store aromatic hydrocarbons that have a high degree of structural similarity, including structural and positional isomers. For example, ortho-xylene, meta-xylene, para-xylene, and ethylbenzene can be effectively separated from a mixture of any of the foregoing by using a MOF of disclosure.

The disclosure also provides an apparatus and method for separating one or more aromatic hydrocarbon components from a multi-component mixture comprising aromatic hydrocarbons using a separation system having a feed side and an effluent side separated by one of more MOFs of the disclosure. The apparatus may comprise a column separation format.

"Catalytic Reforming Process" refers to a chemical process used to convert petroleum refinery naphthas distilled from crude oil (typically having low octane ratings) into high-octane liquid products called reformates, which are premium blending stocks for high-octane gasoline. Reformates are highly enriched with aromatic hydrocarbons. A MOF of the disclosure can be used as an effective adsorbent for aromatic hydrocarbons. In a certain embodiment, a MOF disclosed herein can be used to separate and/or store one or more aromatic hydrocarbons generated via a catalytic reforming process.

In a particular embodiment, one or more MOFs disclosed herein are part of a device. In another embodiment, an aromatic hydrocarbon separation device comprises one or more MOFs of the disclosure. In a further embodiment, an aromatic hydrocarbon separation device used to separate one or more aromatic hydrocarbons from an aromatic hydrocarbon mixture comprises one or more MOFs disclosed herein. Examples of aromatic hydrocarbon separation and/or aromatic hydrocarbon separation devices include, but are not limited to, purifiers, filters, scrubbers, pressure swing adsorption devices, molecular sieves, hollow fiber membranes, ceramic membranes, cryogenic air separation devices, and hybrid aromatic hydrocarbon separation devices. In a certain embodiment, an aromatic hydrocarbon separation device comprising one or more MOFs of the disclosure is used to separate isomers of an aromatic hydrocarbon (e.g., xylene) from an aromatic hydrocarbon mixture. In another embodiment, an aromatic hydrocarbon separation device comprising one or more MOFs of the disclosure is used to separate aromatic products (e.g., reformates) from a catalytic reforming process.

In a particular embodiment of the disclosure, an aromatic hydrocarbon storage material comprises one or more MOFs disclosed herein. Aromatic hydrocarbons that may be stored or separated by the methods, compositions and systems of the disclosure includes xylene, toluene, benzene, ethylbenzene, mesitylene, durene, 2-phenylhexane, biphenyl, phenol, aniline, nitrobenzene, benzoic acid, naphthalene, anthracene, phenanthrene, and any combination of the foregoing. In a particularly useful variation of a gas storage material disclosed herein is an aromatic hydrocarbon storage material that is used to store aromatic hydrocarbons produced via a catalytic reforming processes (i.e., reformates).

The disclosure also provides methods using one or more MOFs disclosed herein. In a certain embodiment, a method to separate or store one or more aromatic hydrocarbons comprises contacting one or more aromatic hydrocarbons with one or more MOFs of the disclosure. In a further embodiment, a method to separate or store one or more aromatic hydrocarbons from a mixed aromatic hydrocarbon mixture comprises contacting the aromatic hydrocarbon mixture with one or more MOFs disclosed herein. In a certain embodiment, a method to separate or store one or more aromatic hydrocarbons from catalytic reforming processes comprises contacting reformates with one or more MOFs disclosed herein. In a further embodiment, a method to separate or store aromatic hydrocarbons from a catalytic reforming processes comprises contacting reformates with one or more MOFs disclosed herein. In a certain embodiment, a method to separate or store one or more aromatic hydrocarbons from naphtha or low molecular weight hydrocarbon feedstock comprises contacting the feedstock with one or more MOFs disclosed herein.

The following examples are intended to illustrate but not limit the disclosure. While they are typical of those that might be used, other procedures known to those skilled in the art may alternatively be used.

Examples

Materials

Methanol (MeOH) was purchased from commercial vendors, further dried over molecular sieves and deoxygenated by purging with $N_2$. All other reagents were purchased from commercial vendors and used without further purification, unless otherwise noted. The $H_4$(m-dobdc) ligand was synthesized according to Li et al. (Chin. Chem. Lett. 15:1039 (2005)).

Synthesis of $Co_2$(dobdc) and $Co_2$(m-dobdc).

$Co_2$(dobdc) was synthesized, solvent exchanged, and activated according to a previously reported method that produced single crystals, which were used for all experiments. Briefly, for synthesis of $Co_2$(m-dobdc), to 80 mL of a mixed solvent (50% MeOH by volume in dimethylformamide (DMF)) was added $H_4$(m-dobdc) (240 mg, 1.2 mmol) and anhydrous $CoCl_2$ (3.0 mmol) in an air filled glove box. The solution was dispensed into 8×20 mL scintillation vials, which were each sealed with a PTFE-lined cap and heated at 120° C. for 18 h. The resulting solid for each sample was submerged in DMF (20 mL), and heated at 70° C. for 24 h. The DMF was decanted and replaced with MeOH (20 mL). The suspension was heated at 70° C. for 4 days, during which the MeOH was replaced every 24 h. The material was activated by heating it at 150° C. under dynamic vacuum on a schlenk line for 12 h, followed by further activation of a small amount of the sample by heating the solid under dynamic vacuum (<10 μbar) at 180° C. for 24 h at a ramp rate of 0.5° C./min. It should be noted that larger scale syntheses of $Co_2$(m-dobdc) was also accomplished by stirring in a round-bottom flask equipped with a reflux condenser at a concentration of 5.04 mmol $H_4$(m-dobdc) and 12.6 mmol $CoCl_2$ in 480 mL solvent. Times and temperatures were identical to the small-scale synthesis, but 100 mL of solvent was used for each exchange. (See, e.g., International Pat. Publ. No. WO2015/066693, incorporated herein by reference for all purposes).

$Co_2$(m-dobdc).

Synthesis yielded a pink solid that turned deep purple upon evacuation. IR (neat): 1600 (s), 1555 (s), 1484 (m), 1451 (m), 1390 (s), 1345 (w), 1284 (s), 1167 (s), 1088 (w), 886 (w), 869 (w), 736 (m), 629 (s); Anal. Calcd for $C_8H_2Co_2O_6$: C, 30.80; H, 0.65. Found: C, 31.60; H, 0.68.

$Co_2$(m-dobdc) was synthesized as a microcrystalline powder, which was used for single-component isotherms and breakthrough experiments, and as single crystals according to the following method. Solid 2,4-dihydroxy-isophthalic acid (0.482 g, 2.43 mmol; $H_4$(m-dobdc)) and $Co(NO_3)_2 \cdot 6 H_2O$ (2.38 g, 8.18 mmol) were added to a 500 mL Pyrex jar along with 200 mL of a 1:1:1 DMF:ethanol:

H₂O mixture. The jar was sonicated to dissolved the solids, then sparged with $N_2$ for 1 h. The jar was capped and placed in an oven at 100° C. for 24 h. The solvent was decanted from the resultant single crystals and replaced with DMF, in which the crystals were soaked for 12 h at 120° C. The DMF was replaced and the crystals were again soaked for 12 h at 120° C., which was then repeated one additional time. The DMF was then replaced with methanol, in which the crystals were soaked for 12 h periods at 60° C. The methanol was replaced each cycle and the crystals again heated at 60° C. for a total of 5 cycles. The crystals were then isolated and activated at 180° C. under vacuum for 24-48 h.

Single-Component Isotherm Measurements.

A sample of about 100 mg of either $Co_2$(dobdc) or $Co_2$(m-dobdc) (microcrystalline powder) was placed in an ASAP tube equipped with a Transeal. The samples were activated at 180° C. for 24-48 h under vacuum on a Micromeritics ASAP 2420. They were subsequently transferred to a Micromeritics 3Flex instrument on which the single-component isotherms were measured, with the manifold temperature set to 45° C. For each measurement, the $C_8$ aromatic in question was stored over activated sieves, then placed in a Swagelok sample holder under an inert atmosphere, put on the instrument's vapor dosing port, and degassed using the freeze-pump-thaw method. The liquid was then heated to 35° C. to increase the vapor pressure available for isotherms. The sample in the ASAP tube was placed in Brinkman Instruments furnace that enveloped most of the sample tube and then filled with sand, with metal casings extending from within the top of the sand bath to the top of the tube to ensure there were no cold spots in which the xylene or ethylbenzene could condense. The top of the sand bath was wrapped in glass wool to provide additional insulation, and the port above the sample tube was wrapped in heating tape and heated to about 45° C. Lastly, the temperature of the sand bath was controlled with a temperature probe connected to a Glas-Col DigiTrol II temperature control box. Isotherms were measured in the range of $P/P_0$ from 0-0.9, with $P_0$ set to 15.0 mbar pressure for each xylene with the instrument set to incremental dose mode in increments of 0.1 mmol/g.

Breakthrough Measurements.

Breakthrough measurements were done using a custom-built breakthrough apparatus. $N_2$, the flow of which was controlled by a mass flow controller, was flowed through a mixture of ethylbenzene, o-xylene, m-xylene, and p-xylene in an equimolar composition in the gas phase at a rate of 40 mL/min. The $N_2$ carried this gas phase mixture to a packed bed of either $Co_2$(dobdc) or $Co_2$(m-dobdc) heated to 125° C. in a Brinkman Instruments furnace with temperature control from a Glas-Col DigiTrol II temperature controller. The outlet composition from this packed bed was measured using a Perkin-Elmer Clarus 500 gas chromatograph equipped with a 50 ft×0.02 in Supelco Bentone™ 34/DNDP SCOT capillary column. The GC sampled the outlet flow from the packed bed every 5 min and the relative concentrations of each component of the $C_8$ aromatic mixture were calculated based on the peak areas. After equilibrium was reached during adsorption, desorption was measured by switching the flow through the packed bed to pure $N_2$ at a flow rate of 80 mL/min and increasing the temperature of the packed bed of $Co_2$(dobdc) or $Co_2$(m-dobdc) to 225° C. at a rate of 1° C./min.

In Situ Single-Crystal x-Ray Diffraction Measurements.

A sample of either $Co_2$(dobdc) or $Co_2$(m-dobdc) was soaked in the xylene of interest and subsequently mounted on a single-crystal diffractometer.

Figure 1F:
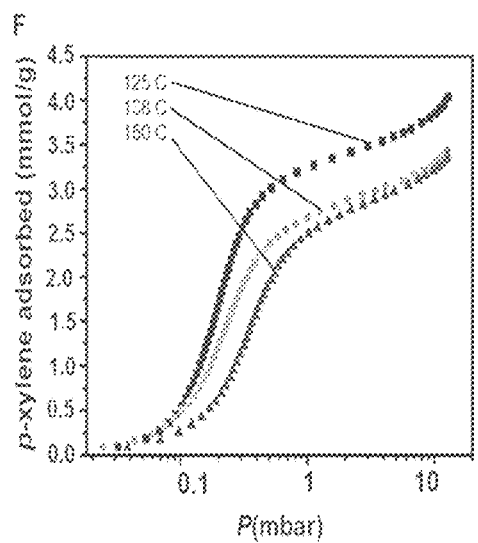

Isotherm Analysis of $Co_2$(dobdc) and $Co_2$(dobpdc) Ability to Distinguish Xylene Isomers:

The isomeric metal-organic frameworks $Co_2$(dobdc) and $Co_2$(m-dobdc) have both been shown to possess 1-D hexagonal channels lined with a high density of five-coordinate cobalt(II) centers. In order to determine the ability of these frameworks to distinguish xylene isomers, single component isotherms (FIG. 1) were collected at 398, 411, and 423 K. Both $Co_2$(dobdc) and $Co_2$(m-dobdc) exhibit a saturation capacity of approximately 3.1 mmol/g for each xylene at 125° C., which is consistent with the binding of one xylene molecule to two metal centers, which corresponds to 3.21 mmol/g uptake. Furthermore, a greater amount of m-xylene is taken up at lower pressures than p-xylene, indicating stronger binding of this isomer to the metal centers in the pores of each metal-organic framework.

Figure 2A:
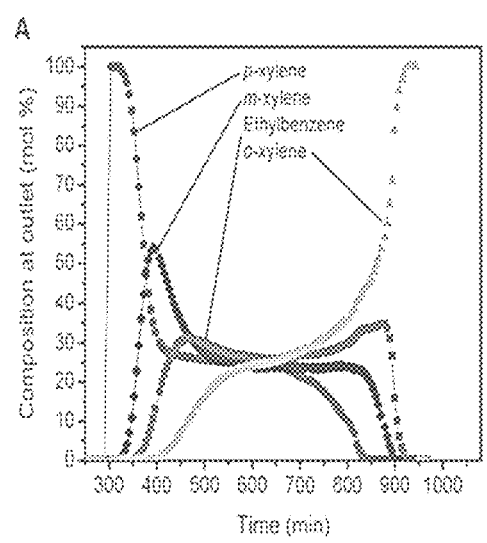
FIG. 2A-B shows breakthrough data for the o-, m-, and p-xylene and ethylbenzene mixture in $Co_2$(dobdc) and $Co_2$(m-dobdc). The four-component mixture is flowed through a packed bed of each metal-organic framework sample and the composition at the outlet is measured with a gas chromatograph. (A) In $Co_2$(dobdc), p-xylene breaks through first, followed by m xylene, ethylbenzene, and finally o-xylene. Subsequent desorption, beginning at about 650 min, follows the same order of elution. (B) A similar breakthrough order is seen in $Co_2(m-dobdc)$, although this material is unable to separate m-xylene and ethylbenzene. Time differences between $Co_2(dobdc)$ and $Co_2(m-dobdc)$ are a result of experimental conditions and material packing in the bed.
Figure 2B:
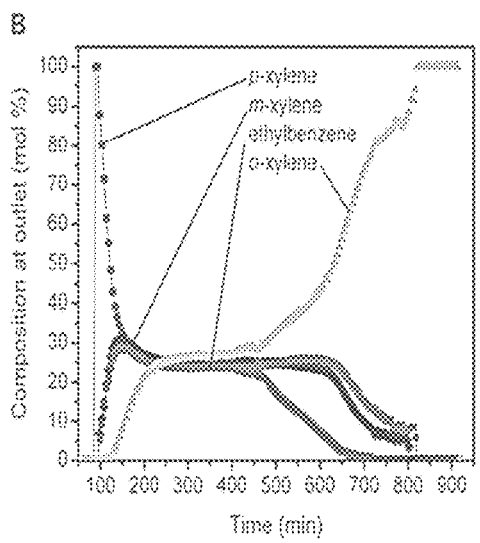

In order to determine how $Co_2$(dobdc) and $Co_2$(m-dobdc) would perform in an actual adsorption-based separation process, breakthrough experiments were performed at elevated temperature. In these experiments, $N_2$ was bubbled through an equimolar mixture of p-xylene, m-xylene, o-xylene, and ethylbenzene and subsequently flowed through approximately 1 g of metal-organic framework sample heated to 125° C. The components of the eluent from this column of sample were determined via GC and plotted as a function of time. As shown in FIG. 2a, p-xylene breaks through the $Co_2$(dobdc) column first, which is reasonable given p-xylene has the lowest heat of adsorption of any of the isomers. This is followed by m-xylene, ethylbenzene, and o-xylene, respectively, until equilibrium is reached; this elution order matches the trend in binding enthalpies seen from single component isotherms. After equilibration, pure nitrogen is flowed through the bed as the temperature is slowly ramped to 498 K. Under these desorption conditions, p-xylene quickly desorbs, again followed by m-xylene, ethylbenzene, and finally o-xylene, with each component desorbing cleanly and separately from the other components. From these results, it is clear that all four $C_8$ isomers can be separated in $Co_2$(dobdc), which has not been shown in metal-organic frameworks previously. Industrially, this could be useful for obtaining all four $C_8$ isomers in one process, which would be especially useful for ethylbenzene production, of which 99% is currently from the reaction of benzene and ethylene.

Interestingly, $Co_2$(m-dobdc), while having a similar structure and equally high density of open metal coordination sites to $Co_2$(dobdc), does not exhibit the same breakthrough behavior for the four component mixture. The p-xylene isomer breaks through first, followed by m-xylene and ethylbenzene simultaneously, with no distinction between these two. As in $Co_2$(dobdc), o-xylene elutes last. While not able to separate all four isomers independently, $Co_2$(m-dobdc) lends itself to current xylenes separation processes, in which the p-xylene and o-xylene are the isomers primarily obtained in separation and m-xylene and ethylbenzene are reisomerized to the equilibrium mixture. $Co_2$(m-dobdc) and its isostructural analogs with other metal cations are also in a prime position among metal-organic frameworks to be used in this application, as the combination of high performance and low cost far outstrips that of other metal-organic frameworks and, at scale, would likely be competitive with the zeolites currently used in xylenes separation processes.

To gain a molecular understanding of the selectivity for $C_8$ separations in these materials, single-crystal x-ray diffraction studies were undertaken. For each experiment, the metal-organic framework sample was exposed to the xylene by soaking the crystals in a liquid sample of the xylene, mounting them on a single crystal diffractometer, and cooling to 100 K for data collection. From the results, it is clear that the interaction of a given xylene molecule with two coordinatively unsaturated metal cation sites is the main contributor to xylene selectivity. The structure of the p-xylene isomer in $Co_2$(dobdc) shows that it is too long to easily fit between two adjacent metal cation sites; as a result, it stacks on the ligand surface and only interacts with a single metal cation site, at a Co . . . $C_{Ar}$ distance of 2.76 Å, which leads to it having the lowest isosteric heat of adsorption and eluting first in the breakthrough experiments. The next isomer to elute, m-xylene, is able to interact with the ligand surface in addition to two adjacent metal cation sites. These interactions are between one Co(II) and one of the m-xylene methyl groups, at a Co . . . $C_{methyl}$ distance of 3.18(4) Å, and the adjacent metal and an aromatic carbon at a Co . . . $C_{Ar}$ distance of 3.03(4) Å (FIG. 3a). The second methyl group simply points into the pore of the framework. The more strongly adsorbed ethylbenzene isomer has a similar interaction in which the benzylic carbon interacts with one metal center at a Co . . . $C_{benzylic}$ distance of 3.345(15) Å, and the aromatic carbon opposite the ethyl group interacts with the second metal center at a Co . . . $C_{Ar}$ distance of 2.948(10) Å (FIG. 3b). The o-xylene isomer exhibits similar behavior to the m-xylene isomer in that one methyl group and the aromatic carbon opposite it interact with the two Co(II) centers at a Co . . . $C_{methyl}$ distance of 3.112 (18) Å and a Co . . . $C_{Ar}$ distance of 2.780 (18) Å, which are closer distances than the other isomers, while the remaining methyl group points into the pore of the framework (FIG. 3c). The o-xylene isomer also has two other binding sites which are discussed below.

Figure 4A:
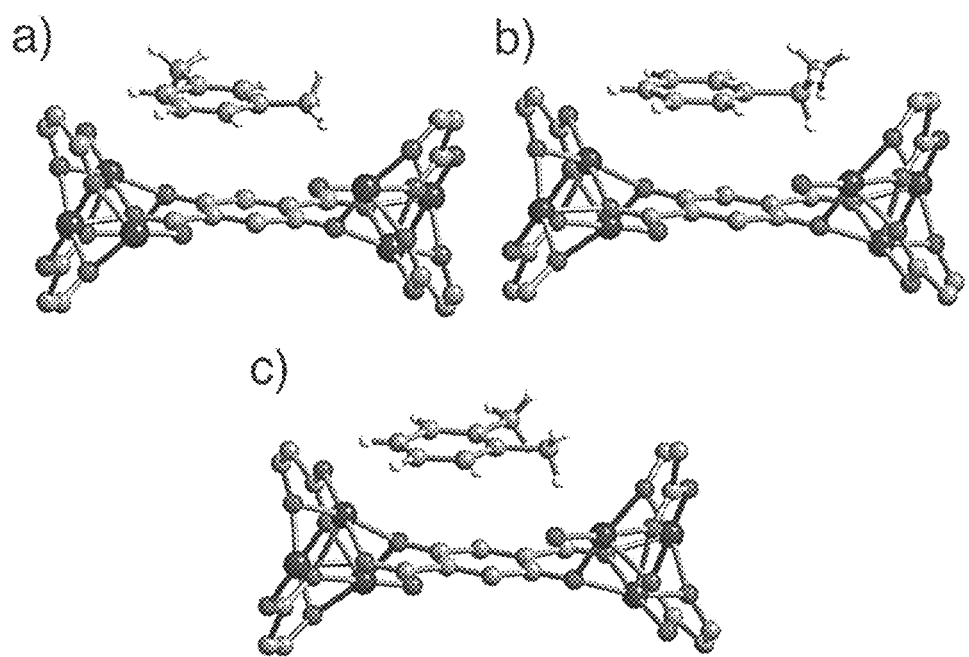
FIG. 4A-B shows in situ single-crystal x-ray diffraction structure in $Co_2(m-dobdc)$. (A) Ethylbenzene bound in the pores of $Co_2(m-dobdc)$, showing the interaction of the aromatic ring of ethylbenzene with one Co(II) center and the $CH_2$ group of the ethyl functionality interacting with a second metal center. (B) o-xylene binding in $Co_2(m-dobdc)$ showing the interaction of each o-xylene molecule with two metal centers, via an interaction of the aromatic ring of the o-xylene molecule with one metal center and one of the methyl groups in o-xylene with the other metal center.
Figure 4B:
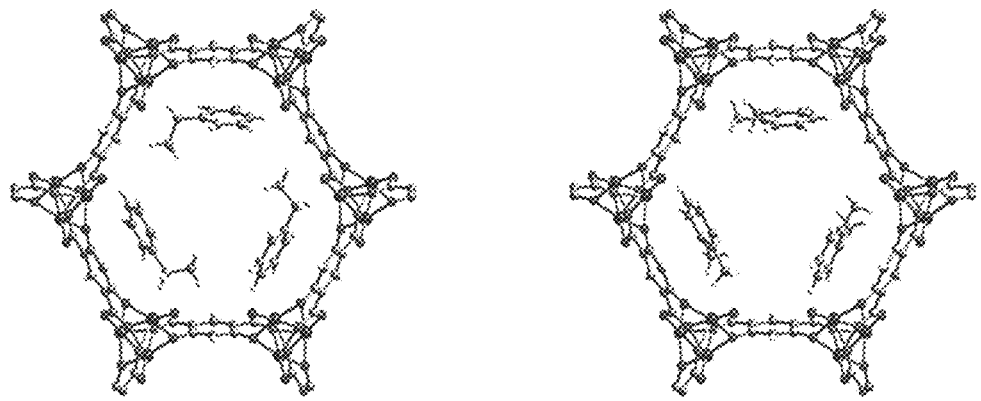

The interactions of o-xylene and ethylbenzene have also been studied using in situ single-crystal x-ray diffraction. FIG. 4 shows the structure of ethylbenzene and o-xylene bound in $Co_2$(m-dobdc).

Figure 5:
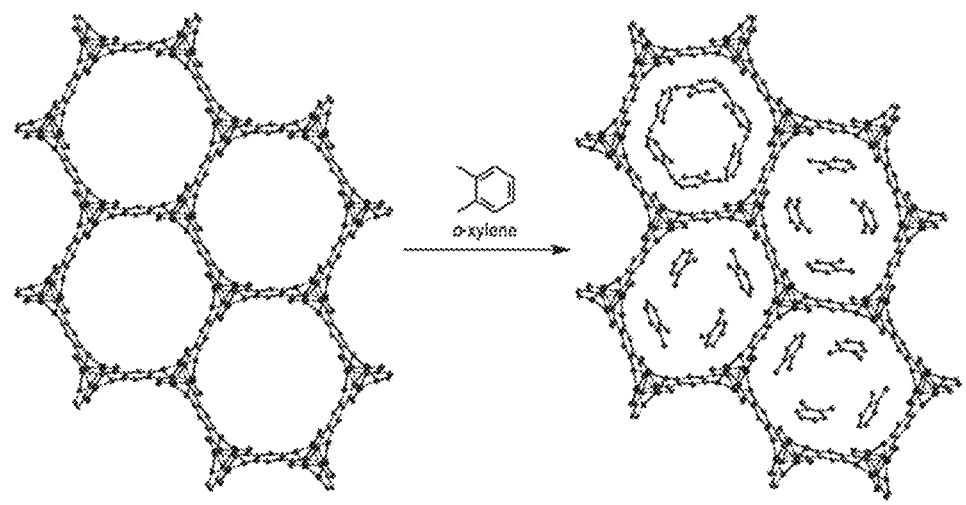
FIG. 5 shows pore flexing upon o-xylene binding in $Co_2(dobdc)$. The pore flexing upon o-xylene binding in $Co_2(dobdc)$ is shown, with the flexing moving the Co(II) centers about 0.2 Å closer together. Bound o-xylene in $Co_2(m-dobdc)$ does not show the same pore flexing, with $Co_2(m-dobdc)$ having adjacent Co(II) centers at the optimal distance prior to o-xylene binding.
Figure 6:
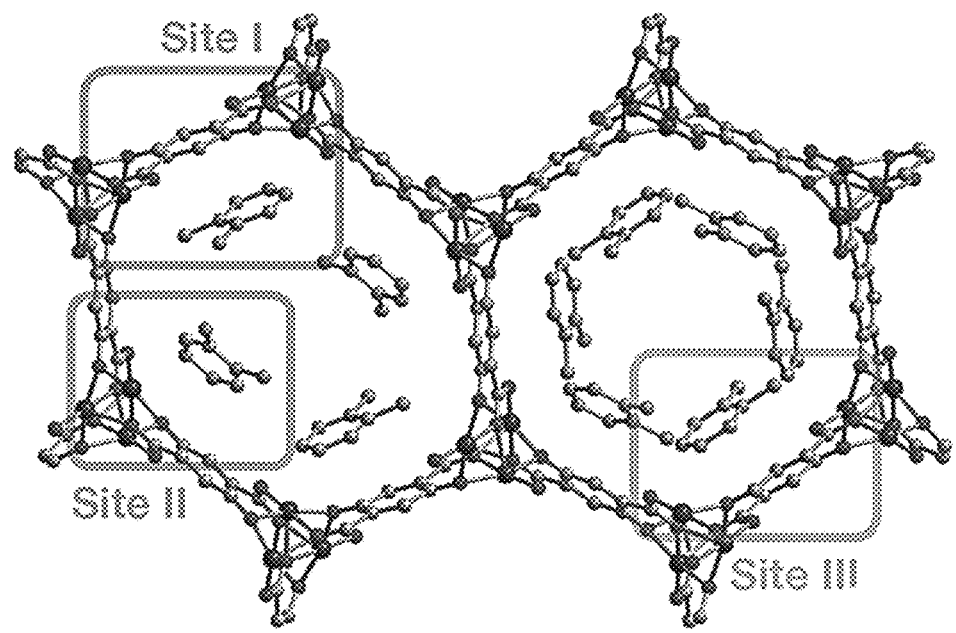
FIG. 6 shows three o-xylene binding sites in $Co_2(dobdc)$. The pore flexing upon o-xylene binding in $Co_2(dobdc)$ is shown, with the flexing moving the Co(II) centers about 0.2 Å closer together. Bound o-xylene in $Co_2(m-dobdc)$ does not show the same pore flexing, with $Co_2(m-dobdc)$ having adjacent Co(II) centers at the optimal distance prior to o-xylene binding.

Most notable, however, is that the structure of $Co_2$(dobdc) is actually flexible upon binding either ethylbenzene or o-xylene. As $Co_2$(dobdc) is typically viewed as a highly rigid metal-organic framework, this framework flexibility is unprecedented in the $M_2$(dobdc) series. The induced structural transformation sees three out of every four pores elongate to accommodate two ethylbenzene or o-xylene molecules along opposite pore walls, with the fourth pore not changing and showing partial occupancy of ethylbenzene or o-xylene on all six pore walls (FIG. 5). Interestingly, the $Co_2$(m-dobdc) framework displays none of the structural flexibility seen in $Co_2$(dobdc) upon binding any of the $C_8$ aromatics. Upon careful consideration of the structures, it can be seen that induced structural transformation in $Co_2$(dobdc) moves the adjacent Co(II) centers 0.2 Å closer together, from 8.04 Å to 7.85 Å, leading to a binding pocket more optimal for binding either ethylbenzene or o-xylene. Due to symmetry differences in $Co_2$(m-dobdc) as compared to $Co_2$(dobdc), the adjacent Co(II) centers are 7.795 Å apart in $Co_2$(m-dobdc), already close to the optimal distance from each other. Due to the flexible nature of the $Co_2$(dobdc) structure upon o-xylene binding, there are three distinct binding sites within the pores of the framework. These can be seen in FIG. 6.

The ability of these isomers to pack in the pores is strongly correlated with their binding enthalpy; p-xylene binds weakly due to its interaction with a single metal center, which is a result of p-xylene being unable to fit in the pocket between the two metal centers. The m-xylene isomer is able to fit in this pocket and interact with both metal centers, but the other methyl group points down the pore and precludes efficient packing of the m-xylene molecules down the c-axis. Ethylbenzene and o-xylene bind most strongly because the $CH_3$ group in the ethyl substituent and the second aromatic methyl group, respectively, don't prevent packing down the c-axis as the methyl group does in m-xylene. Furthermore, the structural flexibility seen in $Co_2$(dobdc) as a result of guest binding is unprecedented for the $M_2$(dobdc) and contributes significantly to the stronger binding of ethylbenzene and o-xylene.

Figure 7:
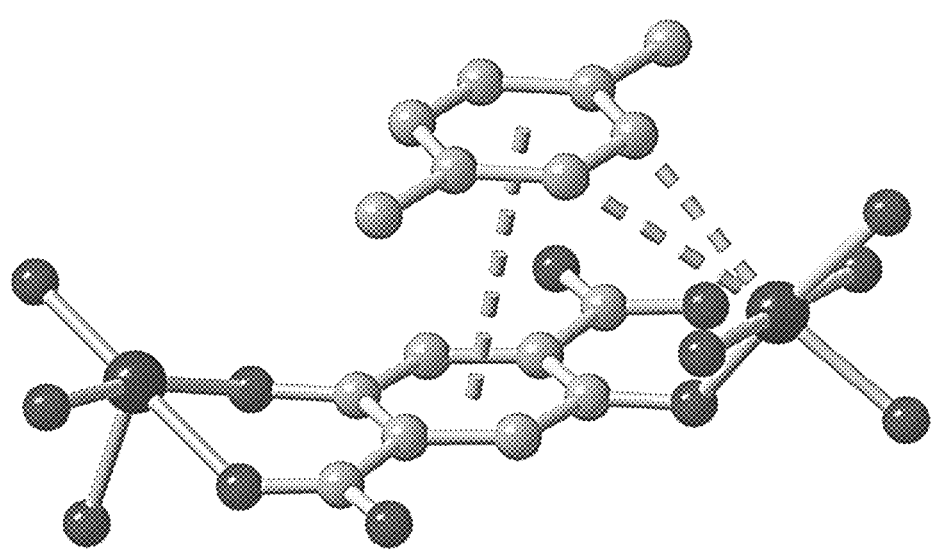
FIG. 7 illustrates the structure of para-xylene in $Co_2$(dobdc).
Figure 8:
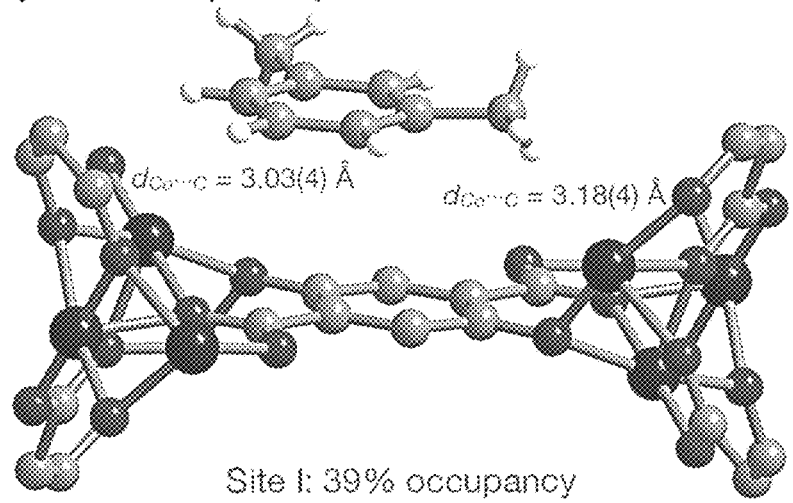
FIG. 8 illustrates the structure of meta-xylene in $Co_2$(dobdc).
Figure 9:
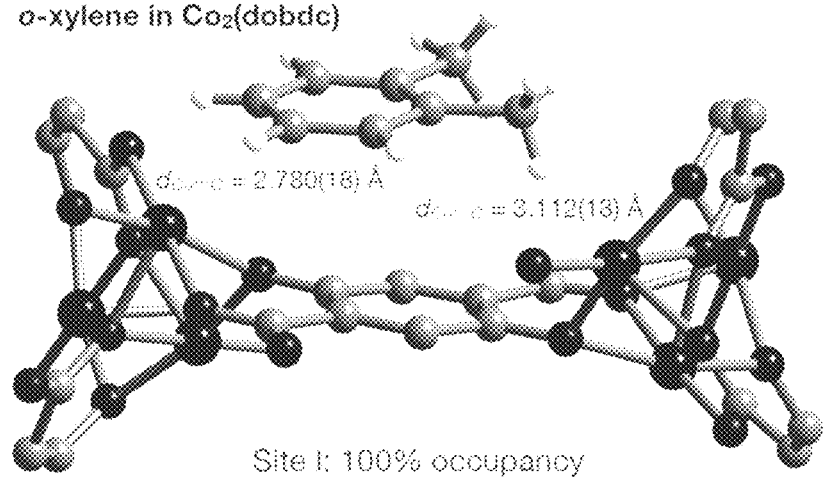
FIG. 9 illustrates the structure of ortho-xylene in $Co_2$(dobdc).
Figure 10:
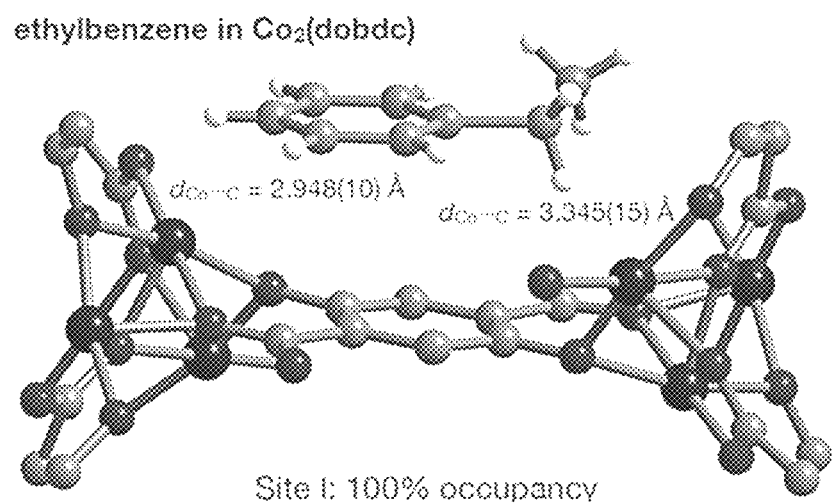
FIG. 10 illustrates the structure of ethylbenzene in $Co_2$(dobdc).
Figure 11A:
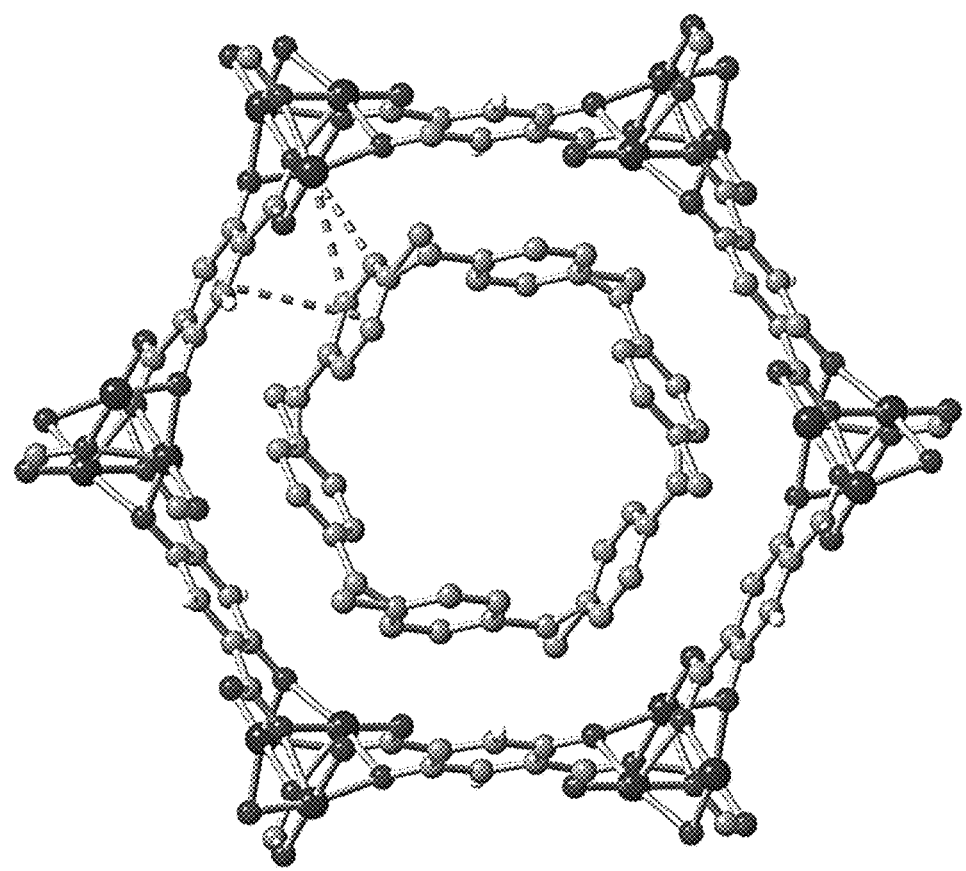
FIG. 11A-D illustrates a single pore of $Co_2(dobdc)$ with (A) para, (B-C) ortho or (D) ethylbenzene adsorbed, illustrating the adsorbate induced flexibility of the material.
Figure 11B:
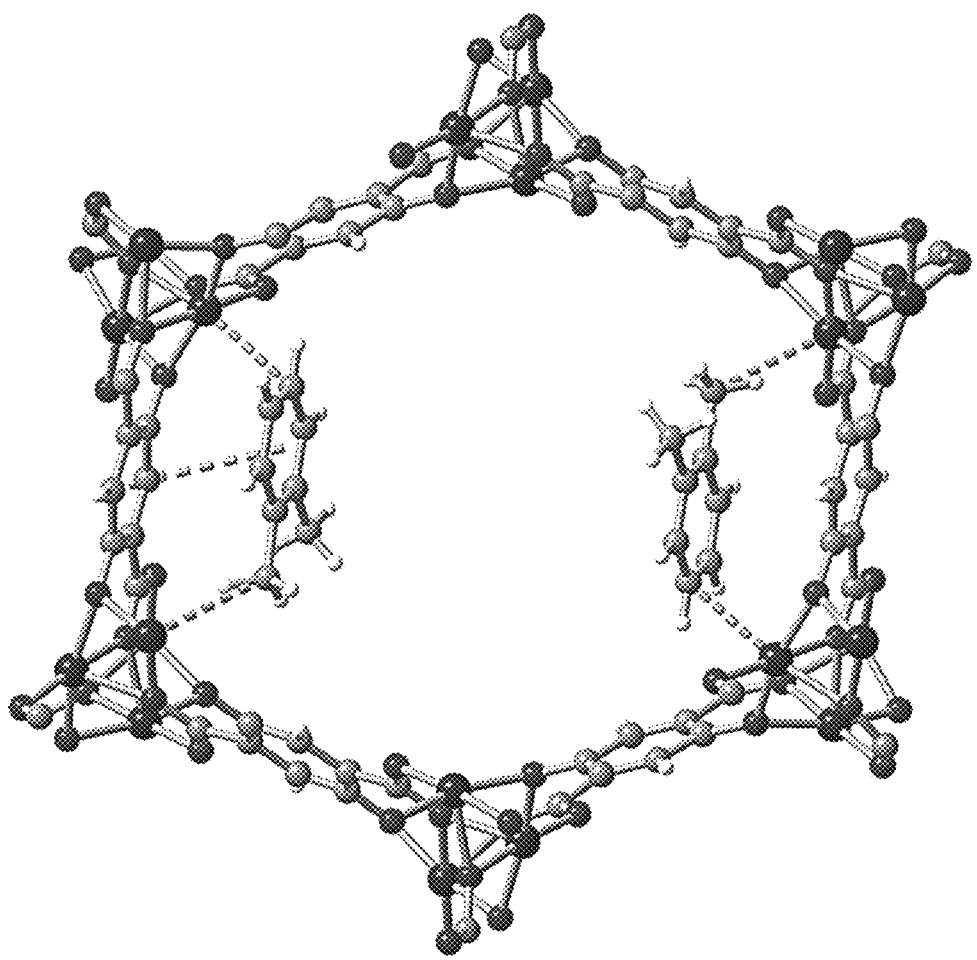
Figure 11C:
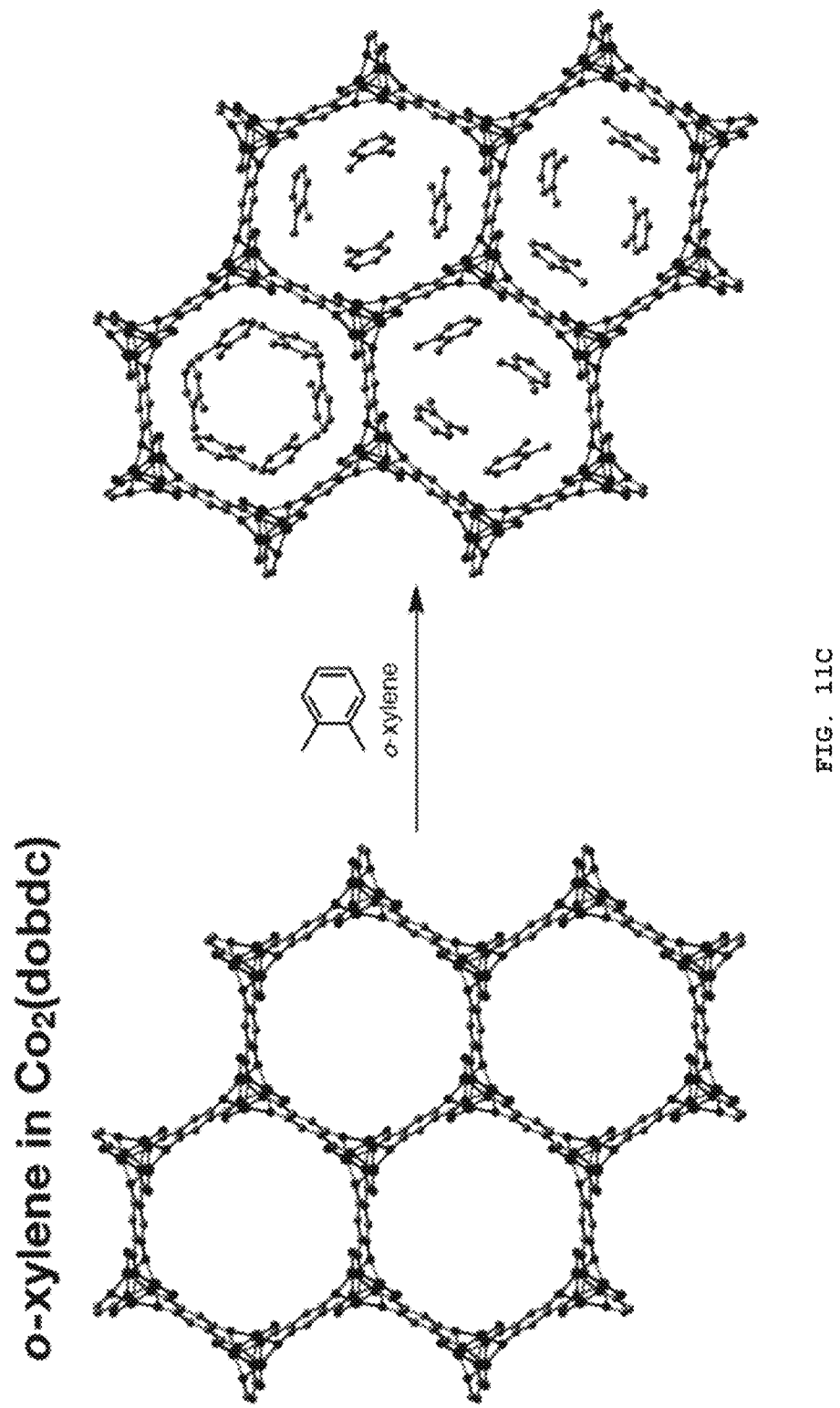
Figure 11D:
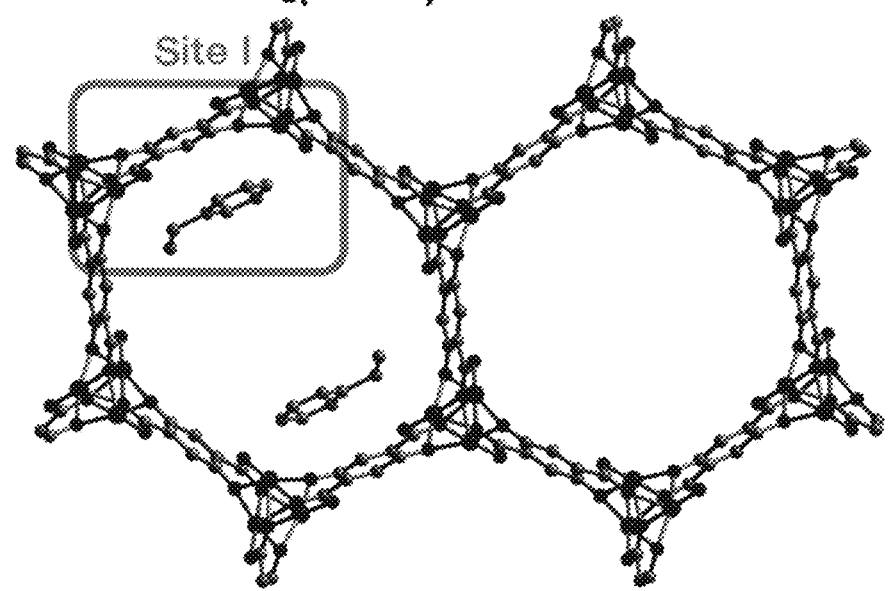

X-Ray Diffraction Experiments Performed with $Co_2$(dobdc):

To determine the exact mechanism of $C_8$ aromatic selectivity, single-crystal X-ray diffraction experiments were performed. In a typical experiment, desolvated crystals of $Co_2$(dobdc) were exposed to a specific $C_8$ isomer vapor, mounted on a single crystal diffractometer, and cooled to 100 K for data collection. From single-crystal results it was clear that the interaction of specific xylene isomers with multiple coordinatively-unsaturated metal cation sites was the main driver for xylene selectivity (see FIGS. 7-9). In the case of para-xylene the molecule was too long to easily fit between two metal cation sites. As a result it stacks on the ligand surface and only interacts with one metal site. Accordingly, this isomer showed the lowest isosteric heat of adsorption and eluted first in the breakthrough experiment. The next isomer to elute, meta, was able to interact with the ligand surface in addition to two adjacent metal cation sites. Finally, the most strongly adsorbed molecules, EB and ortho, not only interacted with the ligand surface and two adjacent metal cations, they induced a structural flexing that brought two metal cations closer together by 0.2 Å, resulting in an even stronger framework-hydrocarbon interaction (see FIG. 11).

Figure 12:
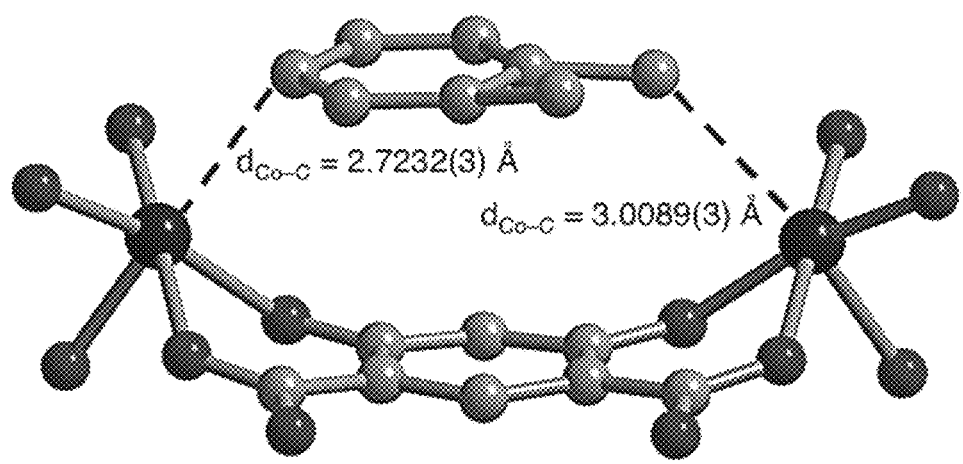
FIG. 12 illustrates the structure of o-xylene bound in $Co_2(m-dobdc)$ from single-crystal x-ray diffraction. Gray, dark gray, and larger black spheres represent C, O, and Co atoms, respectively.

Breakthrough Adsorption Experiments with $Co_2$(m-dobdc):

The known structural isomer of $Co_2$(dobdc), $CO_2$(m-dobdc), has also been shown to effect the separation of mixtures of o-xylene, m-xylene, p-xylene, and ethylbenzene. Interestingly, the separation occurs differently than that of $Co_2$(dobdc), in that the four isomers were not fully separated. In breakthrough experiments, the compounds eluted in the order of para, meta and EB coelution, and ortho last (see FIG. 12). The desorption order was the same as that seen in the effluent during adsorption, with p-xylene breaking through and completely desorbing first, followed by m-xylene and ethylbenzene approximately simultaneously, with desorption of 100% o-xylene at the end of the experiment until the column was completely purged of any residual isomers.

This difference in separation from that seen in $Co_2$(dobdc) is most likely due to the difference in distance between the adjacent metal centers that function as the primary site of interaction for all of these isomers. In the $Co_2$(m-dobdc) framework, this distance is 7.712 Å, while that in $Co_2$(dobdc) is 7.97(6) Å, as determined by x-ray diffraction. This difference in binding between these two framework isomers, $Co_2$(dobdc) and $Co_2$(m-dobdc), was highlighted by the different binding of o-xylene in these two frameworks; the shortest Co . . . C distances in $Co_2$(m-dobdc) for the metal from the aromatic ring and the closest methyl group are 2.7232(3) Å and 3.0089(3) Å, respectively (see FIG. 12). These distances in $Co_2$(dobdc) are 2.751 Å and 3.104 Å, respectively. These differences in binding based on the change in the distance between metal centers highlights the importance of controlling the M . . . M distance in order to control the binding of components of the xylene mixture within the pores of these metal-organic frameworks. Porous metal-organic framework materials could subsequently be designed to better optimize this distance to affect even higher selectivities in separation of the isomers.

A number of embodiments have been described herein. Nevertheless, it will be understood that various modifications may be made without departing from the spirit and scope of this disclosure. Accordingly, other embodiments are within the scope of the following claims.

What is claimed is:

1. A metal-organic framework (MOF) comprising a repeating core having the general structure M-L-M, wherein M is a metal or metal ion, and L is a linking moiety comprising a structure of Formula III:

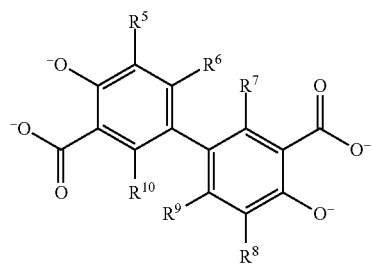

Formula (III)

wherein, $R^5$-$R^{10}$ are independently selected from H, D, FG, optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$)cycloalkyl, optionally substituted ($C_1$-$C_{12}$)cycloalkenyl, optionally substituted aryl, optionally substituted heterocycle, optionally substituted mixed ring system, —C($R^{11}$)$_3$, —CH($R^{11}$)$_2$, —CH$_2$$R^{11}$, —C($R^{12}$)$_3$, —CH($R^{12}$)$_2$, —CH$_2$$R^{12}$, —OC($R^{11}$)$_3$, OCH($R^{11}$)$_2$, —OCH$_2$$R^{11}$, —OC($R^{12}$)$_3$, —OCH($R^{12}$)$_2$, OCH$_2$$R^{12}$;

$R^{11}$ is selected from FG, optionally substituted ($C_1$-$C_{12}$) alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, hemiacetal, hemiketal, acetal, ketal, and orthoester; and $R^{12}$ is selected from one or more substituted or unsubstituted rings selected from cycloalkyl, aryl and heterocycle;

wherein the MOF comprises coordinatively-unsaturated metal cation sites, and wherein the MOF is a selective adsorbent for aromatic hydrocarbons by having multiple unsaturated metal cation sites that can come into contact with an aromatic hydrocarbon to form multiple metal site-hydrocarbon molecule interactions.

2. The MOF of claim 1, wherein the MOF comprises a repeating core having the general structure M-L-M, wherein M is a metal or metal ion, and L is a linking moiety comprising a structure of Formula III:

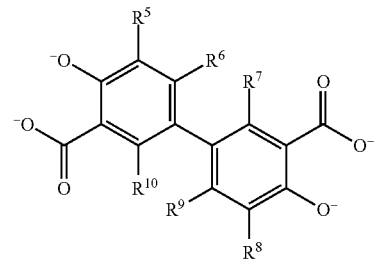

Formula (III)

wherein, $R^5$-$R^{10}$ are independently selected from H, halo, amino, amide, imine, azide, methyl, cyano, nitro, nitroso, hydroxyl, aldehyde, carbonyl, ester, thiol, sulfinyl, sulfonyl, and thiocyanate.

3. The MOF of claim 1, wherein M is selected from L$^+$, Na$^+$, K$^+$, Rb$^+$, Cs$^+$, Be$^{2+}$, Mg$^{2+}$, Ca$^{2+}$, Sr$^{2+}$, Ba$^{2+}$, Sc$^{3+}$, Sc$^{2+}$, Sc$^+$, Y$^{3+}$, Y$^{2+}$, Y$^+$, Ti$^{4+}$, Ti$^{3+}$, Ti$^{2+}$, Zr$^{4+}$, Zr$^{3+}$, Zr$^{2+}$, Hf$^{4+}$, Hf$^{3+}$, V$^{5+}$, V$^{4+}$, V$^{3+}$, V$^{2+}$, Nb$^{5+}$, Nb$^{4+}$, Nb$^{3+}$, Nb$^{2+}$, Ta$^{5+}$, Ta$^{4+}$, Ta$^{3+}$, Ta$^{2+}$, Cr$^{6+}$, Cr$^{5+}$, Cr$^{4+}$, Cr$^{3+}$, Cr$^{2+}$, Cr$^+$, Cr, Mo$^{6+}$, Mo$^{5+}$, Mo$^{4+}$, Mo$^{3+}$, Mo$^{2+}$, Mo$^+$, Mo, W$^{6+}$, W$^{5+}$, W$^{4+}$, W$^{3+}$, W$^{2+}$, W$^+$, W, Mn$^{7+}$, Mn$^{6+}$, Mn$^{5+}$, Mn$^{4+}$, Mn$^{3+}$, Mn$^{2+}$, Mn$^+$, Re$^{7+}$, Re$^{6+}$, Re$^{5+}$, Re$^{4+}$, Re$^{3+}$, Re$^{2+}$, Re$^+$, Re, Fe$^{6+}$, Fe$^{4+}$, Fe$^{3+}$, Fe$^{2+}$, Fe$^+$, Fe, Ru$^{8+}$, Ru$^{7+}$, Ru$^{6+}$, Ru$^{4+}$, Ru$^{3+}$, Ru$^{2+}$, Os$^{8+}$, Os$^{7+}$, Os$^{6+}$, Os$^{5+}$, Os$^{4+}$, Os$^{3+}$, Os$^{2+}$, Os$^+$, Os, Co$^{5+}$, Co$^{4+}$, Co$^{3+}$, Co$^{2+}$, Co$^+$, Rh$^{6+}$, Rh$^{5+}$, Rh$^{4+}$, Rh$^{3+}$, Rh$^{2+}$, Rh$^+$, Ir$^{6+}$, Ir$^{5+}$, Ir$^{4+}$, Ir$^{3+}$, Ir$^{2+}$, Ir$^+$, Ir, Ni$^{3+}$, Ni$^{2+}$, Ni$^+$, Ni, Pd$^{6+}$, Pd$^{4+}$, Pd$^{2+}$, Pd$^+$, Pd, Pt$^{6+}$, Pt$^{5+}$, Pt$^{4+}$, Pt$^{3+}$, Pt$^{2+}$, Pt$^+$, Cu$^{4+}$, Cu$^{3+}$, Cu$^{2+}$, Cu$^+$, Ag$^{3+}$, Ag$^{2+}$, Ag$^+$, Au$^{5+}$, Au$^{4+}$, Au$^{3+}$, Au$^{2+}$, Au$^+$, Zn$^{2+}$, Zn$^+$, Zn, Cd$^{2+}$, Cd$^+$, Hg$^{4+}$, Hg$^{2+}$, Hg$^+$, B$^{3+}$, B$^{2+}$, B$^+$, Al$^{3+}$, Al$^{2+}$, Al$^+$, Ga$^{3+}$, Ga$^{2+}$, Ga$^+$, In$^{3+}$, In$^{2+}$, In$^{1+}$, Tl$^{3+}$, Tl$^+$, Si$^{4+}$, Si$^{3+}$, Si$^{2+}$, Si$^+$, Ge$^{4+}$, Ge$^{3+}$, Ge$^{2+}$, Ge$^+$, Ge, Sn$^{4+}$, Sn$^{2+}$, Pb$^{4+}$, Pb$^{2+}$, As$^{5+}$, As$^{3+}$, As$^{2+}$, As$^+$, Sb$^{5+}$, Sb$^{3+}$, Bi$^{5+}$, Bi$^{3+}$, Te$^{6+}$, Te$^{5+}$, Te$^{4+}$, Te$^{2+}$, La$^{3+}$, La$^{2+}$, Ce$^{4+}$, Ce$^{3+}$, Ce$^{2+}$, Pr$^{4+}$, Pr$^{3+}$, Pr$^{2+}$, Nd$^{3+}$, Nd$^{2+}$, Sm$^{3+}$, Sm$^{2+}$, Eu$^{3+}$, Eu$^{2+}$, Gd$^{3+}$, Gd$^{2+}$, Gd+, Tb$^{4+}$, Tb$^{3+}$, Tb$^{2+}$, Tb+, Db$^{3+}$, Db$^{2+}$, Ho$^{3+}$, Er$^{3+}$, Tm$^{4+}$, Tm$^{3+}$, Tm$^{2+}$, Yb$^{3+}$, Yb$^{2+}$, Lu$^{3+}$, La$^{3+}$, La$^{2+}$, La$^+$, and combinations thereof, including any complexes which contain the metals or metal ions, as well as any corresponding metal salt counter-anions.

4. The MOF of claim 3, wherein M is selected from Be$^{2+}$, Mg$^{2+}$, Ca$^{2+}$, Sr$^{2+}$, Ba$^{2+}$, Sc$^{2+}$, Y$^{2+}$, Ti$^{2+}$, Zr$^{2+}$, V$^{2+}$, Nb$^{2+}$, Ta$^{2+}$, Cr$^{2+}$, Mo$^{2+}$, W$^{2+}$, Mn$^{2+}$, Re$^{2+}$, Fe$^{2+}$, Ru$^{2+}$, Os$^{2+}$, Co$^{2+}$, Rh$^{2+}$, Ir$^{2+}$, Ni$^{2+}$, Pd$^{2+}$, Pt$^{2+}$, Cu$^{2+}$, Ag$^{2+}$, Au$^{2+}$, Zn$^{2+}$, Cd$^{2+}$, Hg$^{2+}$, B$^{2+}$, Al$^{2+}$, Ga$^{2+}$, In$^{2+}$, Si$^{2+}$, Ge$^{2+}$, Sn$^{2+}$, Pb$^{2+}$, As$^{2+}$, Te$^{2+}$, La$^{2+}$, Ce$^{2+}$, Pr$^{2+}$, Nd$^{2+}$, Sm$^{2+}$, Eu$^{2+}$, Gd$^{2+}$, Tb$^{2+}$, Db$^{2+}$, Tm$^{2+}$, Yb$^{2+}$, and La$^{2+}$, including any complexes which contain the metal ions, as well as any corresponding metal salt counter-anions.

5. The MOF of claim 4, wherein M is Co$^{2+}$.

6. The MOF of claim 1, wherein the MOF comprises a repeating core of Co$_2$(dobpdc) (dobpdc=4,4'-dioxido-3,3'-biphenyldicarboxylate).

7. The MOF of claim 1, wherein the MOF comprises 1-D hexagonal channels with a high density of 5-coordinate metal centers with a sixth, vacant coordination site pointing into the pores.

8. The MOF of claim 1, wherein the MOF is reacted with a post framework reactant that adds at least one effect to a MOF selected from:

modulating the aromatic hydrocarbon storage and/or separation ability of the MOF;

modulating the sorption properties of the MOF;

modulating the pore size of the MOF; and modulating the metal-metal separation distance of the MOF.

9. A device comprising a MOF of claim 1 used for separating and/or storing aromatic hydrocarbons.

10. A method of separating and/or storing one or more aromatic hydrocarbons from a mixture comprising aromatic hydrocarbons comprising contacting the mixture with a MOF comprising a repeating core having the general structure M-L-M, wherein M is a metal or metal ion, and L is a linking moiety comprising a structure of Formula I, II and/or Formula III:

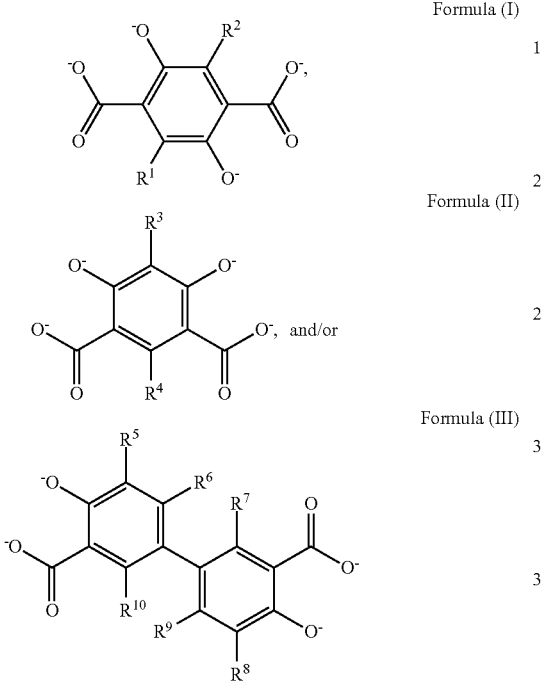

Formula (I)

Formula (II)

Formula (III)

wherein,
R$^1$-R$^{10}$ are independently selected from H, D, FG, optionally substituted (C$_1$-C$_{12}$)alkyl, optionally substituted hetero-(C$_1$-C$_{12}$)alkyl, optionally substituted (C$_1$-C$_{12}$)alkenyl, optionally substituted hetero-(C$_1$-C$_{12}$)alkenyl, optionally substituted (C$_1$-C$_{12}$)alkynyl, optionally substituted hetero-(C$_1$-C$_{12}$)alkynyl, optionally substituted (C$_1$-C$_{12}$)cycloalkyl, optionally substituted (C$_1$-C$_{12}$)cycloalkenyl, optionally substituted aryl, optionally substituted heterocycle, optionally substituted mixed ring system, —C(R$^{11}$)$_3$, —CH(R$^{11}$)$_2$, —CH$_2$R$^{11}$, —C(R$^{12}$)$_3$, —CH(R$^{12}$)$_2$, —CH$_2$R$^{12}$, —OC(R$^{11}$)$_3$, OCH(R$^{11}$)$_2$, —OCH$_2$R$^{11}$, —OC(R$^{12}$)$_3$, —OCH(R$^{12}$)$_2$, OCH$_2$R$^{12}$;

R$^{11}$ is selected from FG, optionally substituted (C$_1$-C$_{12}$) alkyl, optionally substituted hetero-(C$_1$-C$_{12}$)alkyl, optionally substituted (C$_1$-C$_{12}$)alkenyl, optionally substituted hetero-(C$_1$-C$_{12}$)alkenyl, optionally substituted (C$_1$-C$_{12}$)alkynyl, optionally substituted hetero-(C$_1$-C$_{12}$)alkynyl, hemiacetal, hemiketal, acetal, ketal, and orthoester; and R$^{12}$ is selected from one or more substituted or unsubstituted rings selected from cycloalkyl, aryl and heterocycle;

wherein the MOF comprises coordinatively-unsaturated metal cation sites, and wherein the MOF is a selective adsorbent for aromatic hydrocarbons by having multiple unsaturated metal cation sites that can come into contact with an aromatic hydrocarbon to form multiple metal site-hydrocarbon molecule interactions.

11. The method of claim 10, wherein the mixture comprises reformates from a catalytic reforming process.

12. The method of claim 10, wherein the mixture comprises aromatic hydrocarbons selected from toluene, ethylbenzene, benzene, para-xylene, meta-xylene, ortho-xylene, durene, mesitylene, biphenyl, naphthalene, anthracene, phenanthrene, and any combination thereof.

13. The method of claim 12, wherein the mixture comprises aromatic hydrocarbons selected from ethylbenzene, para-xylene, meta-xylene, and ortho-xylene.

14. The method of claim 10, wherein the MOF comprises a repeating core having the general structure M-L-M, wherein M is a metal or metal ion, and L is a linking moiety comprising a structure of Formula I, II and/or Formula III:

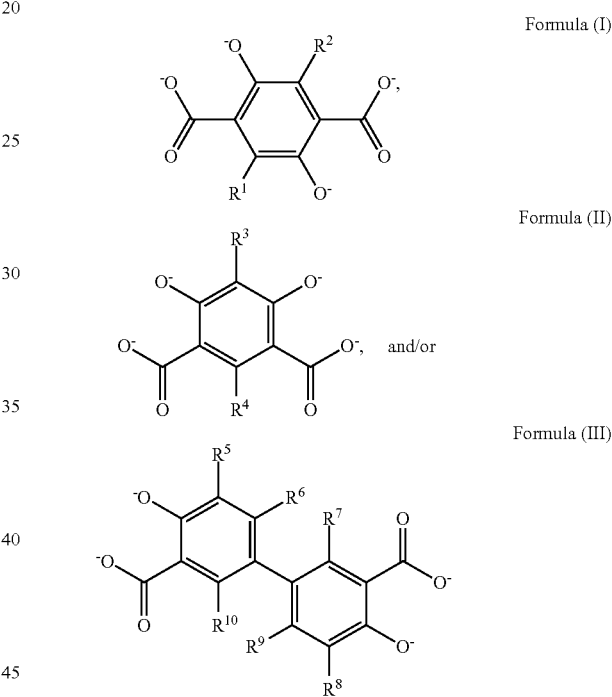

Formula (I)

Formula (II)

Formula (III)

wherein,
R$^1$-R$^{10}$ are independently selected from H, halo, amino, amide, imine, azide, methyl, cyano, nitro, nitroso, hydroxyl, aldehyde, carbonyl, ester, thiol, sulfinyl, sulfonyl, and thiocyanate.

15. The method of claim 10, wherein M is selected from Be$^{2+}$, Mg$^{2+}$, Ca$^{2+}$, Sr$^{2+}$, Ba$^{2+}$, Sc$^{2+}$, Y$^{2+}$, Ti$^{2+}$, Zr$^{2+}$, V$^{2+}$, Nb$^{2+}$, Ta$^{2+}$, Cr$^{2+}$, Mo$^{2+}$, W$^{2+}$, Mn$^{2+}$, Re$^{2+}$, Fe$^{2+}$, Ru$^{2+}$, Os$^{2+}$, Co$^{2+}$, Rh$^{2+}$, Ir$^{2+}$, Ni$^{2+}$, Pd$^{2+}$, Pt$^{2+}$, Cu$^{2+}$, Ag$^{2+}$, Au$^{2+}$, Zn$^{2+}$, Cd$^{2+}$, Hg$^{2+}$, B$^{2+}$, Al$^{2+}$, Ga$^{2+}$, In$^{2+}$, Si$^{2+}$, Ge$^{2+}$, Sn$^{2+}$, Pb$^{2+}$, As$^{2+}$, Te$^{2+}$, La$^{2+}$, Ce$^{2+}$, Pr$^{2+}$, Nd$^{2+}$, Sm$^{2+}$, Eu$^{2+}$, Gd$^{2+}$, Tb$^{2+}$, Db$^{2+}$, Tm$^{2+}$, Yb$^{2+}$, and La$^{2+}$, including any complexes which contain the metal ions, as well as any corresponding metal salt counter-anions.

16. The method of claim 15, wherein M is Co$^{2+}$.

17. The method of claim 10, wherein the MOF comprises a repeating core of Co$_2$(dobdc), Co$_2$(m-dobdc) or Co$_2$(dobpdc) (dobdc=2,5-dioxido-1,4-benzenedicarboxylate, m-dobdc=4,6-dioxido-1,3-benzenedicarboxylate, dobpdc=4,4'-dioxido-3,3'-biphenyldicarboxylate).

18. The method of claim 17, wherein the MOF comprises a repeating core of $Co_2(dobdc)$.

19. The method of claim 1, wherein the metal-metal separation distance of the MOF is from about 7.7 Å to about 12.7 Å.

20. The method of claim 10, wherein the MOF comprises 1-D hexagonal channels with a high density of 5-coordinate metal centers with a sixth, vacant coordination site pointing into the pores.

* * * * *